United States Patent
Buckman et al.

(10) Patent No.: US 7,329,792 B2
(45) Date of Patent: Feb. 12, 2008

(54) METHOD AND APPARATUS FOR HEMOSTASIS

(75) Inventors: Robert F. Buckman, Radnor, PA (US); Jay A. Lenker, Laguna Beach, CA (US); Donald J. Kolehmainen, Laguna Niguel, CA (US)

(73) Assignee: Damage Control Surgical Technologies, Inc., Lagune Beach, CA (US)

( * ) Notice: Subject to any disclaimer, the term of this patent is extended or adjusted under 35 U.S.C. 154(b) by 356 days.

(21) Appl. No.: 11/087,224

(22) Filed: Mar. 23, 2005

(65) Prior Publication Data

US 2005/0165445 A1    Jul. 28, 2005

Related U.S. Application Data

(63) Continuation-in-part of application No. 10/358,881, filed on Feb. 4, 2003, now Pat. No. 6,998,510.

(60) Provisional application No. 60/555,537, filed on Mar. 23, 2004.

(51) Int. Cl.
*A61F 13/00* (2006.01)

(52) U.S. Cl. .......................... 602/53; 602/42; 602/43; 602/48; 602/54

(58) Field of Classification Search ........ 606/201–203; 602/41–43, 46, 18, 53; 424/443, 447–449
See application file for complete search history.

(56) References Cited

U.S. PATENT DOCUMENTS

| | | | |
|---|---|---|---|
| 2,344,021 A * | 3/1944 | Bouziane | 606/201 |
| 3,874,387 A * | 4/1975 | Barbieri | 602/53 |
| 4,538,603 A | 9/1985 | Pawelchak et al. | |
| 5,181,914 A | 1/1993 | Zook | |
| 5,330,452 A | 7/1994 | Zook | |
| 5,376,067 A | 12/1994 | Daneshvar | |
| 5,423,736 A | 6/1995 | Cartmell et al. | |
| 5,447,505 A | 9/1995 | Valentine et al. | |
| 5,466,231 A | 11/1995 | Cercone et al. | |
| 5,470,625 A | 11/1995 | Perrault | |
| 5,478,308 A | 12/1995 | Cartmell et al. | |
| 5,538,500 A | 7/1996 | Peterson | |

(Continued)

FOREIGN PATENT DOCUMENTS

WO    WO 00/25726 A2    5/2000

*Primary Examiner*—Kim M Lewis

(57) ABSTRACT

Devices and methods are disclosed for achieving hemostasis in patients who have received skin-penetrating wounds to the periphery, including the head, arms, and legs. Such haemostatic packing devices and methods are especially useful in the emergency, trauma surgery, or military setting. The devices utilize fluid impermeable barriers surrounded by exterior dams and pressure to achieve tamponade and hemostasis, primarily by exertion of force to hold the dams against the skin surrounding a wound. The devices are capable of serving as carriers for thrombogenic, antimicrobial or antipathogenic agents. The devices do not require the use of adhesives to work as they are attached to the patient using mechanical locking devices. Peripheral haemostatic packing devices include optional adhesive hemostatic barriers to attach at least a portion of the device to the skin or to assist with initial coupling of a hold-down strap to another strap using a more secure mechanical lock. The peripheral hemostatic packing system does not completely surround the extremity having the wound and therefore do not cause a tourniquet effect. The peripheral hemostatic packing system preferably is held against the skin surrounding a wound by a force that is generally unidirectional and substantially perpendicular to the plane in which the skin of the wound resides.

20 Claims, 20 Drawing Sheets

U.S. PATENT DOCUMENTS

| | | |
|---|---|---|
| 5,800,372 A | 9/1998 | Bell et al. |
| 5,843,060 A | 12/1998 | Cercone |
| 6,096,943 A | 8/2000 | Maiwald |
| 6,164,279 A | 12/2000 | Tweedle |
| 6,343,604 B1 | 2/2002 | Beall |
| 2002/0029010 A1 | 3/2002 | Augustine et al. |

* cited by examiner

METHOD AND APPARATUS FOR HEMOSTASIS

RELATED APPLICATIONS

The present application claims priority benefit under 35 USC § 119(e) from U.S. Provisional Application No. 60/555,537 filed Mar. 23, 2004, entitled "METHOD AND APPARATUS FOR PERIPHERAL HEMOSTASIS" and is a Continuation-in-Part of U.S. Non-Provisional application Ser. No. 10/358,881 filed Feb. 4, 2003, now U.S. Pat. No. 6,998,510 the entirety of both of which are hereby incorporated herein by reference.

FIELD OF THE INVENTION

The field of this invention is wound care during trauma surgery, general surgery, combat medicine, and emergency medical services. The invention is applicable to animals, especially including mammals, and is directed primarily at use on humans.

BACKGROUND OF THE INVENTION

As recently as the early 1990s, surgical operations for trauma were directed at the anatomic repair of all injuries at time of the initial operation. It was observed during these exercises that many patients became hypothermic, acidotic, and coagulopathic. Patients showing these three signs often died. Death often occurred in the operating room due to exsanguinations, or postoperatively, due to the complications of prolonged shock and massive transfusion to replace blood lost as a result of the trauma.

One of the most notable developments in the recent evolution of surgery has been the introduction of the concept of staged laparotomy to overcome the deficiencies of the repair all-at-once approach. This new strategy of staged laparotomy, employing new tactics that have been termed damage control, is now used in 10% to 20% of all trauma laparotomies.

This damage control strategy opens the way for a variety of new devices and methods for a) control of hemorrhage from solid organs or viscera, b) control of hemorrhage from peripheral wounds and peripheral vascular lacerations, and c) control of contents spillage from hollow viscera. Although there are procedures for controlling these injuries, none of these procedures utilize optimal devices or tactics in their execution. Each area offers technological opportunities to improve the devices and procedures for applying those devices.

Ever since the advent of abdominal surgery, surgeons have relied on the same thinly woven cotton gauze packing pads that are currently in favor. These gauze pads are called laparotomy pads or Mickulitz pads. These pads were designed for use as sponges but not for use as hemostatic tampons. Nonetheless, since World War I, surgeons faced with severe bleeding have relied on packing patients with these sterilizable gauze sponges in an effort to control bleeding. Since World War II, it has been known that abdominal packing using these pads has been associated with abdominal sepsis and re-bleeding after pad removal. Despite these limitations, even today, they are the mainstay of damage control hemostasis.

The specific issues with the gauze pads are that they are porous and allow the free passage of blood through the mesh. Other unfavorable characteristics include the lack of intrinsic coagulation inducing properties. The pads are easily saturated and they do not stick to one another. The pads are capable of promoting infection because they serve as a nidus for bacteria in a contaminated field. They have no intrinsic antiseptic or antimicrobial action. These pads are unsuitable for packing solid viscera because they stick to the visceral wound tissue and cause re-bleeding upon removal. Although generally recognized as sub-optimal, the gauze pads have the advantages of being cheap, familiar and ubiquitous. For these later reasons, they continue to remain the mainstay of damage control hemostasis. Among the opportunities for new technologies and instruments to support the process of damage control, the first requirement is an improvement in the surgical pack and for control of peripheral hemorrhage through an open wound through the skin.

Other current pads for hemostasis include gel-foam, Surgicel, and fibrin sponges. These devices are all liquid permeable and require blood coagulation to occur before impermeability and hemostasis are achieved. In addition, the fibrin sponges are very rigid and will not conform to a wound while in the dry state. Typical examples of the prior art in hemostatic packing systems include U.S. Pat. No. 5,643,596 to Pruss et al., U.S. Pat. No. 5,763,411 to Edwardson et al., U.S. Pat. No. 5,800,372 to Bell et al., U.S. Pat. No. 6,054,122 to MacPhee et al., and U.S. Pat. No. 6,056,970 to Greenawalt et al. These patents, all of which are included herein by reference, disclose permeable hemostatic packing and dressings with topical hemostatic coatings. These devices all serve the purpose of stopping bleeding in underlying vessels with an occlusive backing but the backing is still permeable to blood leakage. The lack of impermeability in these prior art patents is not recognized as an issue.

While hemostatic packing devices are well known in the art, the utility of said packing devices is limited by their propensity to harbor pathogens and their propensity to create re-bleeding by adherence to healing surfaces. One device uses a powdered hemostatic agent that is poured into a wound. The hemostatic agent reacts with the blood, withdrawing water from the blood and causing rapid thrombosis to occur. This agent, however, aggravates the spread of infection and is difficult to remove when definitive repair takes place. The reaction with the blood is exothermic and causes undesirable, localized tissue heating. Further, there is no inherent mechanism to hold the hemostatic agent in place in the wound other than application of a separate covering bandage. In addition, current devices adhere to a wound or surrounding tissue by adhesive methodologies. In an acute or emergency setting there may be profuse bleeding, water, oil, mud, or other contaminants that defeat an adhesive and prevent sticking. Current bandages can control bleeding that weeps from a wound because of pressure restrictions but do not control major vessel hemorrhage because they cannot stop the flow of blood at unrestricted systemic arterial pressure.

New devices, procedures and methods are needed to support the strategy of damage control in patients who have experienced massive bodily injury. Such devices and procedures are particularly important in the emergency, military, and trauma care setting. These new devices rely on the principles of impermeability to blood passage, limited nidus formation for bacteria, the ability to carry prothrombogenic material, and the lack of intrinsic thrombogenicity except by providing a physical barrier or pressure source.

SUMMARY OF THE INVENTION

This invention relates to an improved hemostatic packing device for use in trauma care. The present invention is an impermeable barrier pack or wrap for a body appendage. Other features of the pack include foldability and moldability to the anatomical surface. The exterior surface of the pack is not intrinsically thrombogenic but is capable of serving as a carrier for thrombogenic substances. Said thrombogenic substances can be liquids or solids but are, preferably gels with internal cohesion and spreadability. Certain regions of the exterior surface of the pack may optionally comprise thrombogenic properties. The pack may be made with a plurality of surfaces, each with distinct characteristics. An exemplary version of the pack has a thin layer of polyethylene or polypropylene, which is impermeable to liquids, covering its entire outer surface. A key advantage of the present invention, in its wet or dry state, is moldability, flexibility and shapeability to the anatomical contacting surface, including the ability to pack wounds in solid viscera. The pack is able to distribute pressure within the wound to generate pressure tamponade. The pack is capable of generating pressure tamponade without regions of sharp or high stress such as would be generated by a rigid packing system. This improvement over certain very hard packing devices allows for better fit to the anatomy and the immediate formation of an impermeable barrier without the need to wait for blood coagulation to occur to form the hemostatic barrier. The hemostatic pack of the present invention is placed via open surgery or through laparoscopic instrumentation. The laparoscopic embodiment includes the capability of reversibly or irreversibly achieving a size and mass change in the device once it is placed within the patient.

The present invention distinguishes over the cited prior art because it requires no thrombogenic coatings, although it is capable of trapping and carrying such pro-thrombogenic coatings on its surface. The outer surface of the haemostatic packing sponge serves as a carrier by incorporating indents or villi to physically hold the pharmacological, thrombogenic or antibacterial coatings. Since the surface is impermeable to liquids, the arrest of hemorrhage is immediate and does not require thrombosis to occur. When the packing device of the present invention is removed from the patient, re-bleeding does not occur because there is not penetration of the wound tissues or clot into the interstices of the pack. An additional advantage of the impermeable pack is a resistance to bacteria and other pathogenic penetration.

In another embodiment of the invention, the pack, or wrap, comprises raised ridges or dams on its surface. These ridges or dams are comprised of soft conformable materials that form an edge seal to prevent the escape of blood from a wound. The pack, or wrap, optionally comprises additional regions or borders of enhanced blood clotting or thrombogenesis to assist with the hemostatic properties of the device.

In yet another embodiment of the present invention, the hemostatic pack comprises adhesives, fasteners, or the like to allow the packs to adhere to each other, thus forming a syncytium, or contiguous barrier comprised of more than one component, to prevent blood from escaping from a wound.

In another embodiment of the invention, the hemostatic pack is a bandage or peripheral hemostasis system (PHS) that is worn over a vascular wound that communicates with the exterior environment of the patient through a break in the skin. Such wounds, particularly in the extremities of the patient such as the head, neck, arms, legs, hands, and feet, may include severe vascular damage that could result in bleeding to death, or near-exsanguination with its concomitant complications. In an embodiment, a bandage or PHS is described that comprises one or more external dams that are held against the skin surrounding the wound by force sufficiently capable of sealing the wound from blood leakage. The region inside the dam is bounded by the dams at the perimeter, a liquid impermeable barrier on the exterior, and the skin and wound on the inside. Blood cannot escape from this region as long as the seal between the dam and the skin is intact. This device is most efficacious on patient extremities since the vasculature is typically surrounded by intramuscularly tissue, which cannot be tunneled by blood hemorrhage under systemic arterial pressure to cause blood pooling. In the thorax, abdomen, or pelvic region, internal body cavities can fill with pressurized blood so the hemostatic pack or wrap is less efficacious in these regions.

In yet another embodiment of the invention, the bandage or PHS comprises a strap to hold the dam and fluid or liquid impermeable region over the wound. The strap, in a preferred embodiment comprises some elasticity and further comprises a fastener that is adjustable. The strap, in another embodiment, further comprises a standoff, which is a rigid or semi-rigid member that prevents the strap from circumferentially constricting the appendage around which the strap is wrapped, yet which allows the strap to pull the dam and fluid impermeable region against the tissue surrounding the wound. The dams and liquid impermeable region therebetween are held against the skin by force in substantially one direction only, not a circumferential or radial force. In yet another embodiment, the bandage comprises a central packing device to exert pressure on the wound to facilitate tamponade. This central packing device may be a folded fabric pad, a sac or a bladder filled with liquid, gas, gel, foam, powder, or the like. The central packing device may also simply comprise an externally communicating port that allows gas or liquid to be infused into the region between the dams, the liquid impermeable layer and the skin. The gas or liquid may be pressurized to exceed systemic arterial pressure and thus tamponade the wound. In yet another embodiment of the invention, the bandage comprises an inner dam and an outer dam. A vacuum drawn on the region between the inner dam and the outer dam, through a port that communicates through the fluid impermeable layer between the two dam regions, holds the bandage against the skin and prevents blood escape under systemic arterial pressure.

For purposes of summarizing the invention, certain aspects, advantages and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements.

DETAILED DESCRIPTION OF THE INVENTION

The present invention may be embodied in other specific forms without departing from its spirit or essential characteristics. The described embodiments are to be considered in all respects only as illustrative and not restrictive. The scope of the invention is therefore indicated by the appended claims rather than the foregoing description. All changes that come within the meaning and range of equivalency of the claims are to be embraced within their scope.

Figure 1A:
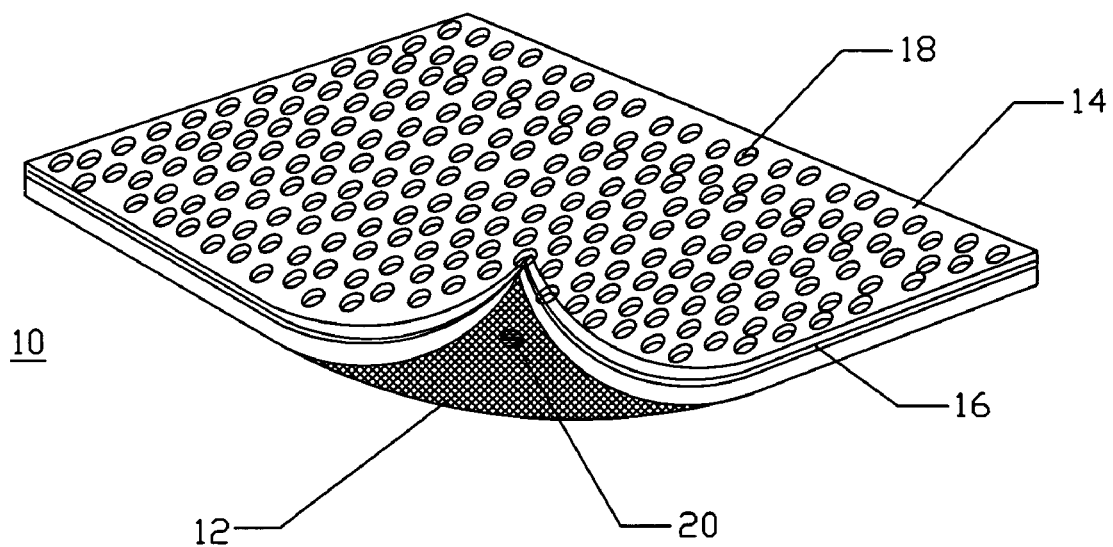
FIG. 1A illustrates a two-sided hemostatic pack comprising a sheet of material that is impermeable to liquid on one side and the other side is a permeable fabric affixed to the impermeable barrier, according to aspects of the invention.

FIG. 1A illustrates a diagram of a two-sided hemostatic packing device 10 of the present invention. The two-sided packing device 10 comprises a substrate 12 and a fluid impermeable surface 14. The fluid impermeable surface 14 further comprises an optional adhesive layer 16, and a plurality of optional indentations 18. The fluid impermeable surface 14 or the substrate 12 may optionally comprise a plurality of radiopaque markers 20.

Referring to FIG. 1A, the hemostatic packing device 10 is a flat sheet configuration that is flexible and deformable. The substrate 12 is a flat sheet configuration and is integral to or affixed to the fluid impermeable surface 14. The adhesive 16 is used to affix the substrate to the fluid impermeable surface. The fluid impermeable surface 14 optionally comprises a plurality of indentations 18. The radiopaque markers 20 may be wire form, dots or patches of barium-impregnated fabrics.

Referring to FIG. 1A, the substrate 12 is fabricated from cotton gauze, open or closed cell foam, sponge, fluids, particulates and the like. The substrate 12 is soft in its wet or dry state and may be bent, molded or deformed to maximize surface contact and force distribution on the injured tissue. The foam configuration of the substrate 12 is fabricated from materials such as polypropylene, polyvinyl chloride, polyurethane, polyethylene, silicone rubber, poly methyl methacrylate, polyvinyl alcohol and the like. The foam configuration of the substrate 12 may be pre-compressed, or partially pre-compressed, to achieve the correct amount of hardness, or it can be fabricated in a plurality of layers. For example, the foam substrate 12 can have an inner layer of hard foam and an outer layer of softer foam. The outer layer of softer foam helps to fill space and conform to irregular geometries while the inner layer of harder foam helps to provide the packing force necessary to overcome systemic arterial pressure. The particulates of the inflatable embodiment of substrate 12 may be beads of collagen, PTFE, silica and the like. The fluid impermeable surface 14 is fabricated from materials such as polypropylene, polyvinyl chloride, polyurethane, polyethylene, silicone rubber, poly methyl methacrylate, polyvinyl alcohol, Tyvek and the like. The fluid impermeable surface 14, in another embodiment, is fabricated from materials such as paper or cloth that is then coated or sprayed with impermeable materials such as polyethylene, polypropylene and the like. The use of rip-stop fabrics will help prevent tearing of the fluid impermeable surface 14.

The hemostatic packing device 10 is fabricated in a variety of sizes and thicknesses. The thickness varies from 0.1 mm to 50 mm. The length and width each may vary from 5 mm to 500 mm. The geometry is generally rectangular but may have triangular, circular, or polygonal configurations. The corners may be square or rounded.

The radiopaque markers 20 are fabricated from a group of materials including but not limited to barium impregnated fabrics or polymers, metal wires, and metal solids. Typical metals used for radiopacity include tantalum, platinum, gold, and the like.

The hemostatic packing device 10 is packaged in a sealed, sterile barrier package and is sterilized using standard techniques such as steam, cobalt radiation, ethylene oxide, electron beam and the like.

Figure 1B:
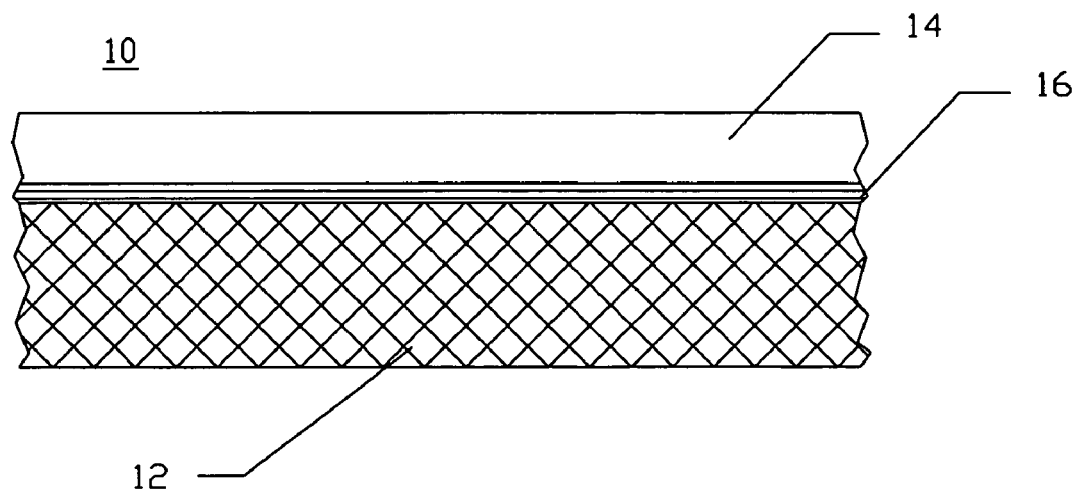
FIG. 1B illustrates a cross-sectional view of the two-sided haemostatic pack, according to aspects of the invention.

Referring to FIG. 1B, the hemostatic packing device 10 is shown from the side. The substrate 12, the fluid impermeable surface 14, and the adhesive layer 16 are clearly visible in this view.

Figure 1C:
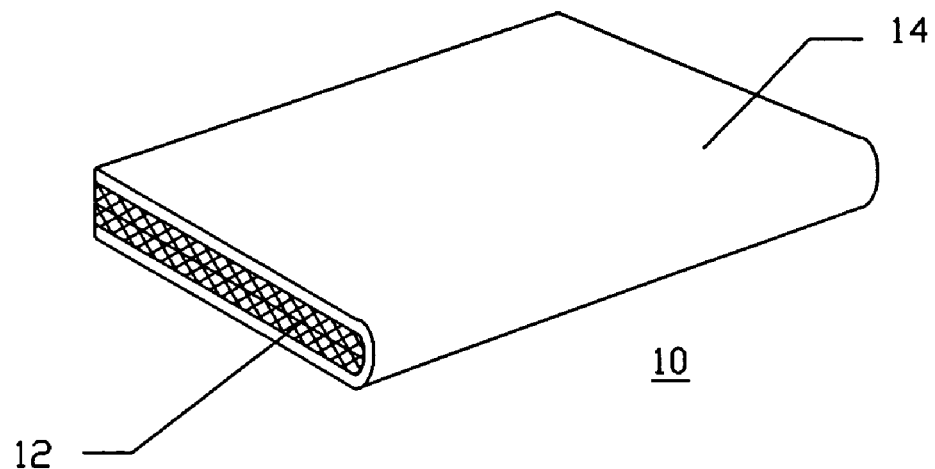
FIG. 1C illustrates the two-sided hemostatic packing device folded with the impermeable surface facing outward toward the wound surface, according to aspects of the invention. In this embodiment the impermeable surface is on both sides of the device.

FIG. 1C illustrates one embodiment of the hemostatic packing device 10 that is folded with the fluid impermeable surface 14 facing outward in preparation for use.

Figure 1D:
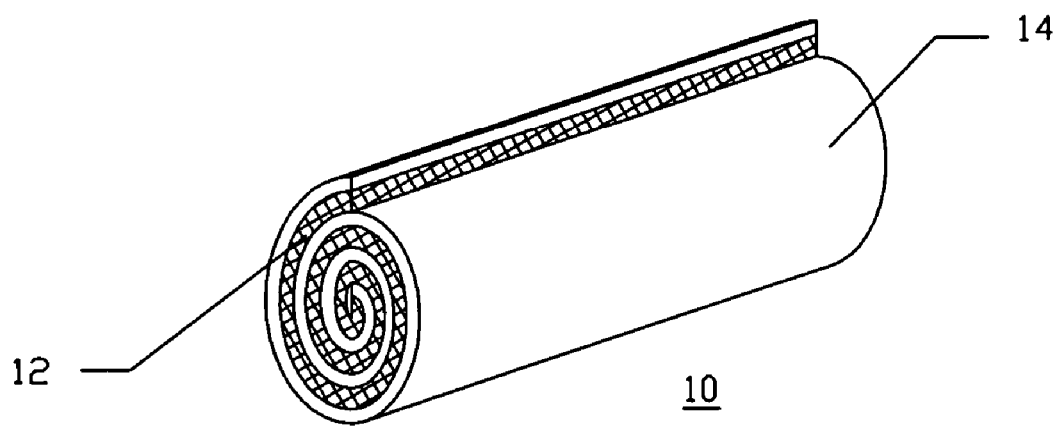
FIG. 1D illustrates the two-sided hemostatic pack rolled with the impermeable side out, according to aspects of the invention.

FIG. 1D illustrates another embodiment of the hemostatic packing device 10 that is rolled with the fluid impermeable surface 14 facing outward in preparation for use.

Figure 2:
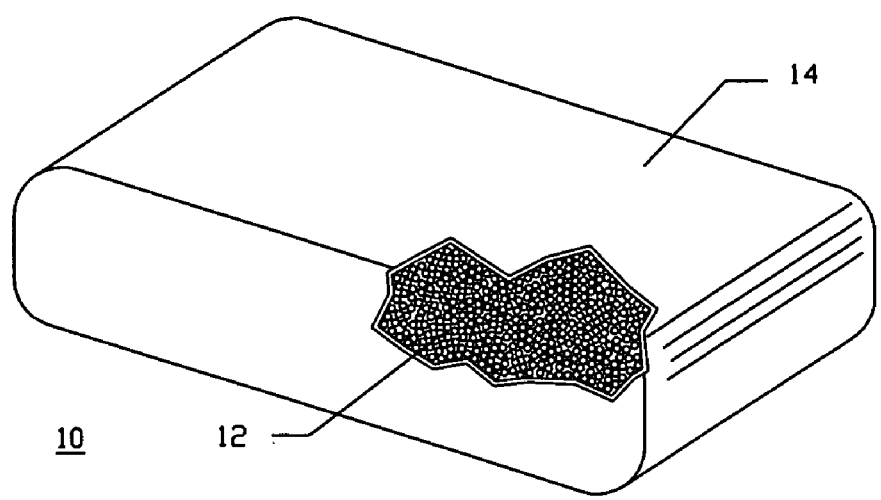
FIG. 2 illustrates a hemostatic packing device comprising a closed-cell foam that is impermeable on both sides, according to aspects of the invention.

FIG. 2 illustrates another embodiment of the haemostatic packing device 10 where the substrate 12 and the impermeable outer surface 14 are fabricated from the same material. In this embodiment, the hemostatic packing device 10 is fabricated from closed-cell foam. The foam material allows for a resilient, deformable substrate while maintaining the outer surface 14 that is impermeable to fluid penetration since it is a closed cell structure.

Figure 3:
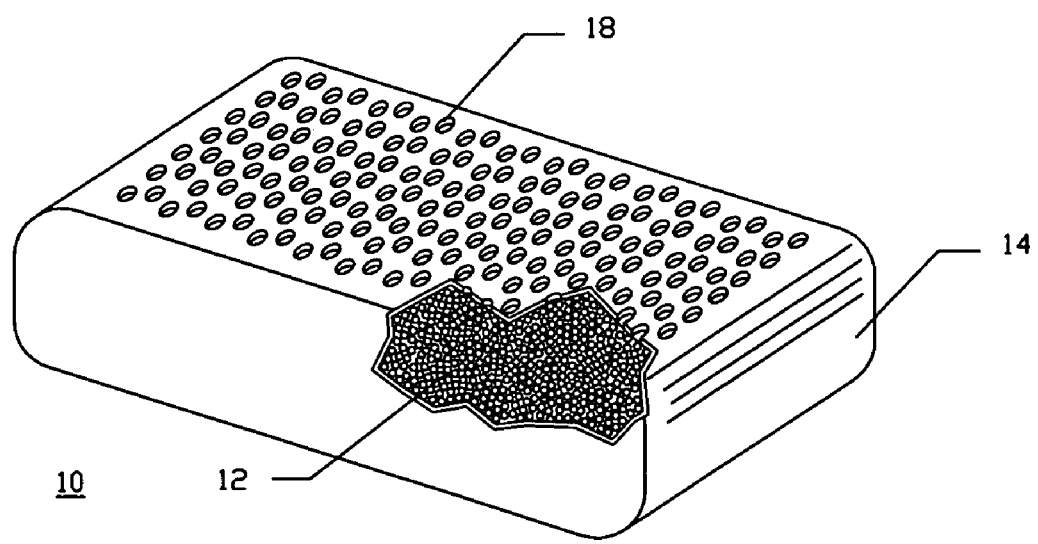
FIG. 3 illustrates a hemostatic packing device comprising an outer surface that is impermeable on both sides where the upper surface further comprises indentations capable of carrying exogenous thrombogenic substances, according to aspects of the invention.

FIG. 3 illustrates the hemostatic packing device 10 where the upper side of the fluid impermeable surface 14 comprises indentations 18, that may be in the form of dimpling or waffling of varying depth that are useful to hold, or carry, and, subsequently deliver thrombogenic, pharmaceutical or antibacterial agents. The indentations 18 are formed using molds wherein the outer surface 14 of the closed-cell substrate 12 is formed against the mold. In another embodiment, the indents 18 are formed by impressing the fluid impermeable outer sheet with a mold or other forming device. In yet another embodiment, the outer surface 14 comprises projections, or villi, that serve to trap and carry the pharmaceutical, antibacterial or thrombogenic agents. The projections or indents may be macroscopic or microscopic.

Figure 4:
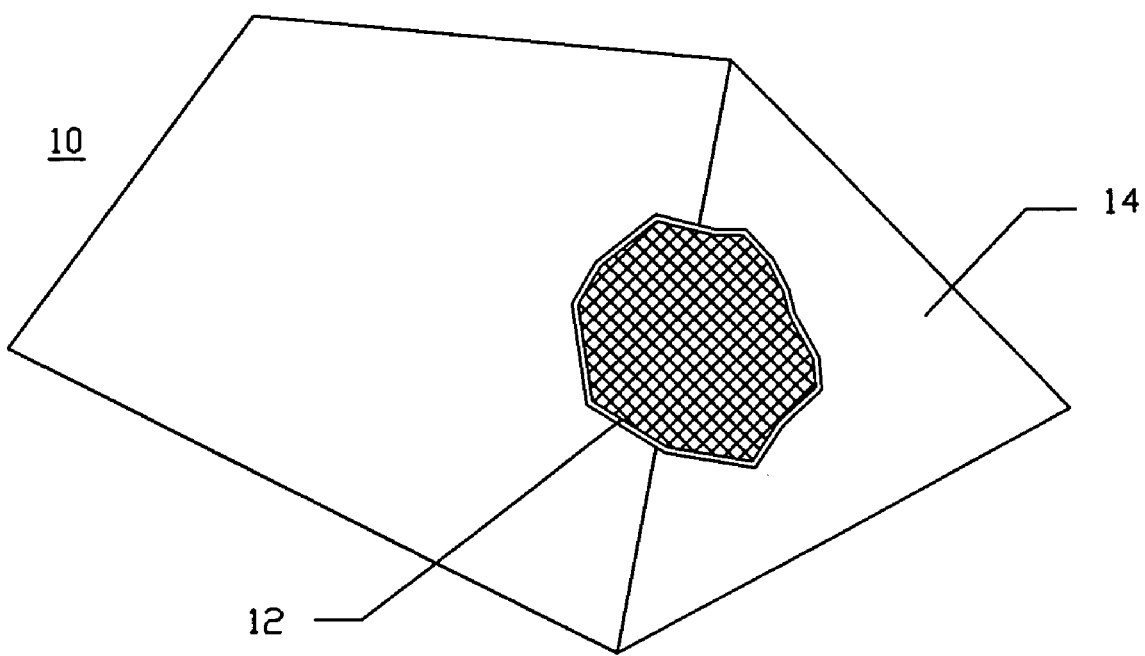
FIG. 4 illustrates a hemostatic packing device comprising a polygonal deformable solid with an impermeable outer surface, according to aspects of the invention.

FIG. 4 illustrates another embodiment of the haemostatic packing device 10 wherein the substrate 12 forms a polygonal solid. The polygonal solids include shapes such as brick or rectangular solid, waffle, pyramid, sheet, and oval. The polygonal solids also include extruded shapes such as cylinders, or extended lengths of cross-sections such as rectangular, oval, circular, trapezoidal, triangular, etc. The lengths of these devices range from 5 mm to 1000 mm. The width dimensions of these devices range from 1 mm to 200 mm. At least part of the outer surface 14 of the hemostatic packing device 10 comprises a fluid impermeable barrier. This fluid impermeable barrier 14 may be smooth, indented, or covered by villi, or projections. The substrate 12 is fabricated from materials that allow for deformation in the dry or wet state. These materials include cotton batting, polymeric foams of varying densities, sand, polymer beads, oils including silicone oils, water, and the like.

Referring to FIGS. 1A, 1B, 1C, 1D, 2, 3, and 4, the hemostatic packing device 10, in another embodiment, comprises a fluid impermeable layer 14 that is fabricated from resorbable materials. The substrate 12 may be removed and the impermeable layer 14 left behind to complete healing. The resorbable layer 14 is fabricated from resorbable materials such as polyglycolic acid (PGA), polylactic acid (PLA) and the like. The fluid impermeable layer 14 has a complex surface that comprises indentations or villi 18.

Figure 5A:
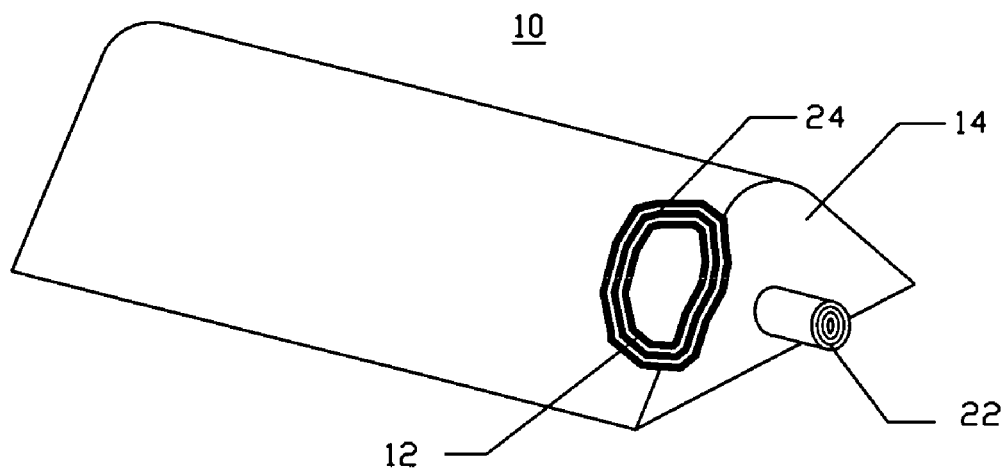
FIG. 5A illustrates an inflatable hemostatic packing device that comprises an impermeable outer surface, and an internal bladder that is capable of containing material, where said material when reversibly introduced into the bladder through a sealing port, is in the form of solid particles, a fluid, or a combination thereof, according to aspects of the invention.
Figure 5B:
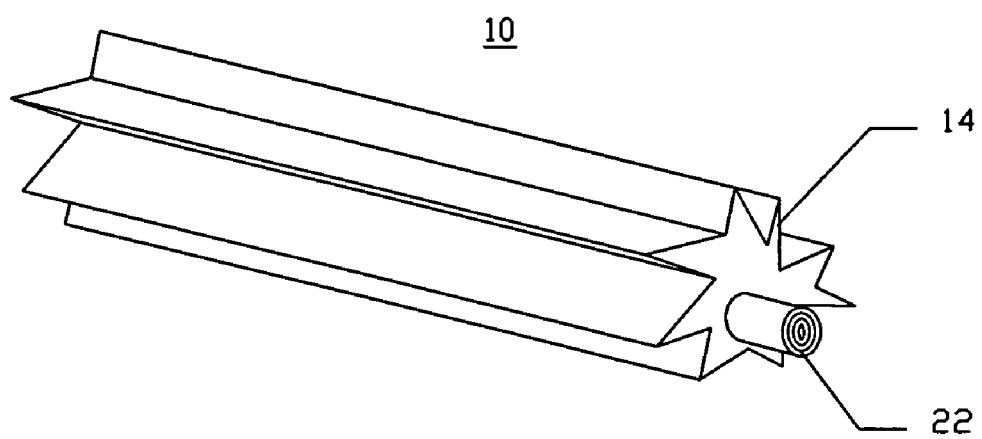
FIG. 5B illustrates one embodiment of the inflatable hemostatic packing device in its deflated or partially deflated state, according to aspects of the invention.

FIG. 5 illustrates yet another embodiment of the hemostatic packing device 10 wherein the device may have fluid reversibly or irreversibly introduced to provide for size adjustment. The outer surface 14 of said device 10 comprises an access port 22 for introduction of materials to fill the substrate 12. In this embodiment, the substrate 12 is a fluid impermeable membrane that is filled with material to achieve the desired volume. The substrate 12 membrane is fabricated either from elastic materials such as silastic or polyurethane, or it is an inelastic bag with folds that allow for size increase. The outer surface of the substrate 12 preferably is not adhered in all places to the outer surface 14 of said device 10 and optionally a lubricating layer 24 is placed between the two structures. The outer surface 14 of said device 10 is fabricated from either elastic materials such as polyurethane or silicone rubber, or it is an inelastic material such as polyethylene terephthalate, polyimide, polypropylene or polyethylene or a copolymer including one of these materials. The outer surface 14 of the hemostatic packing device 10 may be smooth, indented or include villi. The villi or indents may be macroscopic and have size ranges from 0.1 mm to 10 mm. The villi or indents may also be microscopic and difficult to see with the unaided eye. Such sizes are less than 0.1 mm.

Referring to FIG. 5, in another embodiment, the hemostatic packing device 10 comprises a hydrogel material that is placed into a wound and expands upon absorption of fluids from the patient to compress the wound. In this embodiment, the substrate 12 is fabricated from hydrophilic hydrogels such as those described by Park et al. and are incorporated herein by reference. Hydrogels are made from materials such as, but not limited to, carboxymethyl cellulose, cross-linked sodium starch glycolate, and cross-linked polyvinylpyrrolidone and the like. The substrate 12 can also be fabricated from a water-absorbable sponge that expands once it becomes wet. The water-absorbable sponge may be fabricated from materials such as, but not limited to, polyvinyl alcohol, polymethyl cellulose, and the like. In this embodiment, the fluid impermeable outer surface 14 comprises an opening to allow for fluid penetration into the substrate 12 to allow the expansion to occur. This opening may be the nipple 22 and the fluid to expand the hydrogel or sponge may be injected through the nipple 22. Alternatively, in the case of the hydrogel, the substrate 12 and the surface 14 may be of the same hydrogel material. Hydrogels generally absorb water but do not adhere to biological surfaces. The hemostatic packing device 10 fabricated from hydrogel would be small enough in its dry state to be introduced through an optional laparoscopic access port and expand due to water absorption once placed within the body.

Figure 6:
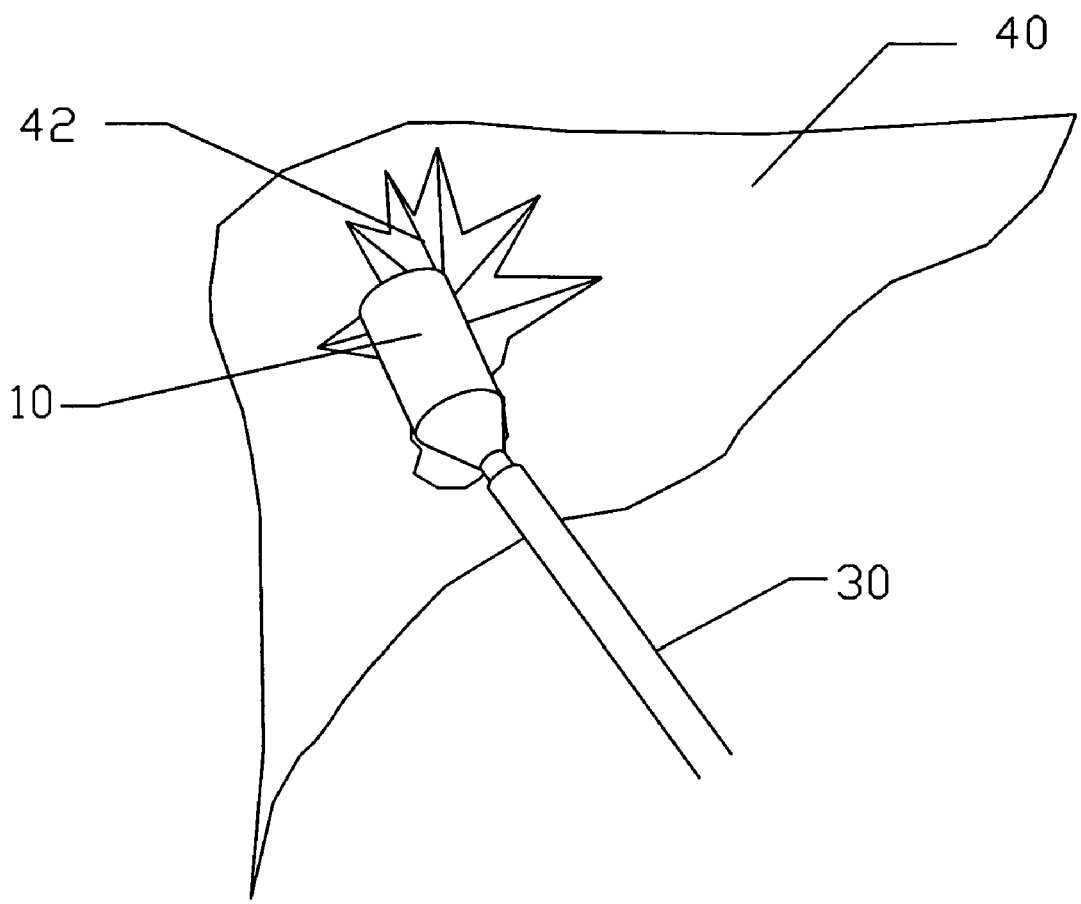
FIG. 6 illustrates a hemostatic packing device being introduced into a patient through a laparoscopic instrument, according to aspects of the invention.

FIG. 6 illustrates the hemostatic packing device 10 being introduced into a wound 42 in a liver 40 through a laparoscopic instrument 30. The laparoscopic instrument 30 is an axially elongate hollow device that provides porthole access to the internal organs of a patient.

Figure 7:
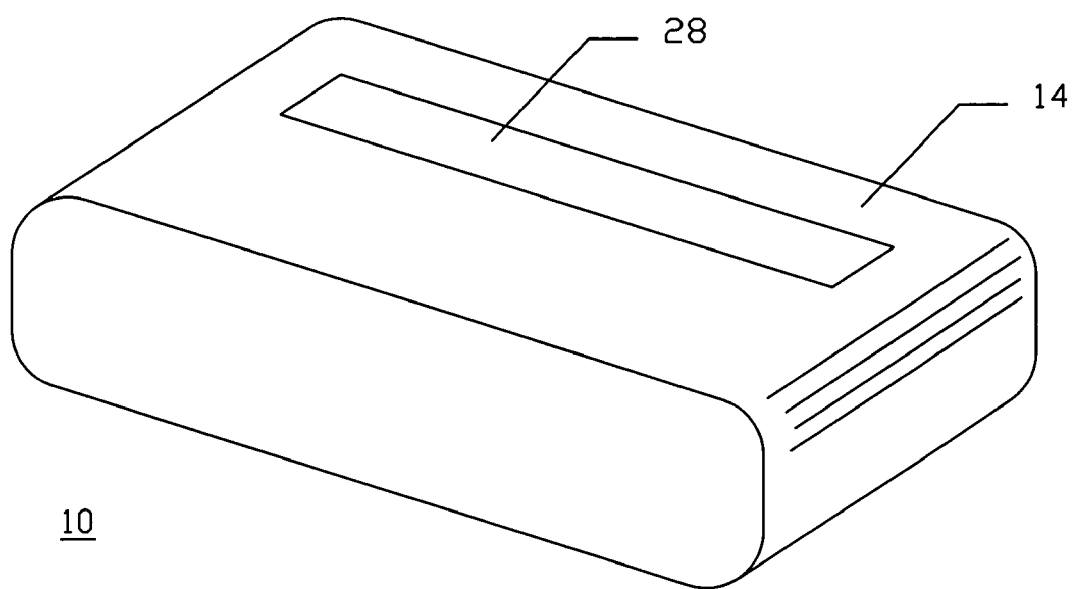
FIG. 7 illustrates a hemostatic packing device comprising an adhesive on at least a portion of the outer impermeable surface of said hemostatic packing device, according to aspects of the invention.

FIG. 7 illustrates the hemostatic packing device 10 comprising an adhesive strip 28 on one side. The adhesive strip 28 is used to permit attachment of the hemostatic packing device 10 to other similar devices so as to create an impermeable syncytium or impermeable contiguous mass. The adhesive strip may also comprise an optional peel away cover that protects the adhesive strip 28 prior to use. The peel away cover is fabricated, preferably, from the same materials use to fabricate the fluid impermeable outer surface 14 of the hemostatic packing device 10. The adhesive strip is optionally fabricated from materials such as Velcro or even self-adhesive materials such as Coban, marketed by 3M. Velcro is a trademark of Dupont and is a hook and loop fastener that is well known in the art.

Figure 8:
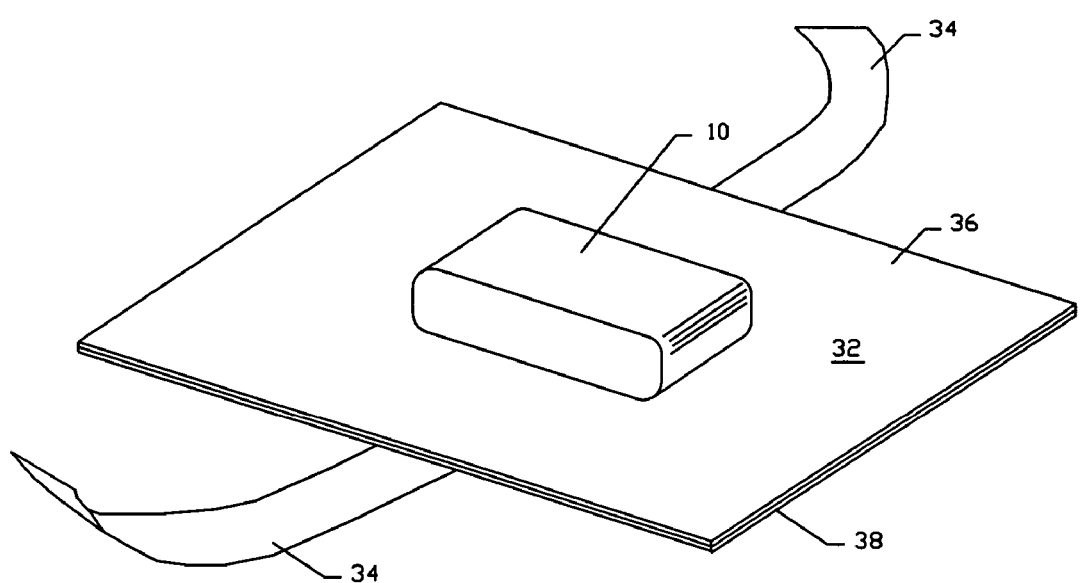
FIG. 8 illustrates a hemostatic packing device comprising a packing material with an impermeable outer surface affixed to an adhesive impermeable drape, according to aspects of the invention.

FIG. 8 illustrates another embodiment of the hemostatic packing device 10 further comprising a fluid impermeable drape 32 affixed to the packing device 10. The fluid impermeable drape 32 is, preferably adhered to the hemostatic packing device 10. The drape 32 comprises an adhesive layer 36 and a backing layer 38. The backing 38 is, preferably, fabricated from non-elastomeric materials such as, but not limited to, polyethylene, polypropylene, and the like. It is preferable that the drape 32 does not stretch once applied. The adhesive layer 36 is on the same side of the drape 32 to which the hemostatic packing device 10 is affixed. The hemostatic packing device 10 further optionally comprises a series of straps 34 to assist with fixation of the device to the patient. The straps 34 are fastened with standard buckles, Velcro or the like. This embodiment of the device 10 is useful for treatment of wounds to the periphery and especially those wounds that involve vascular injury. Such periphery includes the thigh, knee, lower leg, arm, shoulder, and forearm.

Figure 9A:
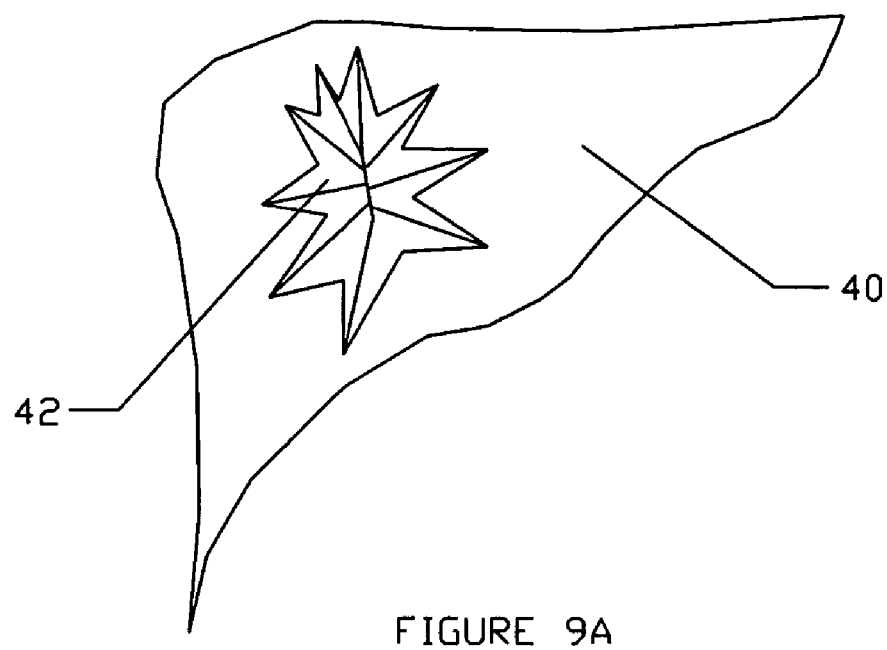
FIG. 9A illustrates a wound of the liver, according to aspects of the invention.

FIG. 9A illustrates the wound 42 to the liver 40. The liver 40 represents an exemplary case of parenchymal tissue that is friable and becomes severely damaged during an abdominal injury.

Figure 9B:
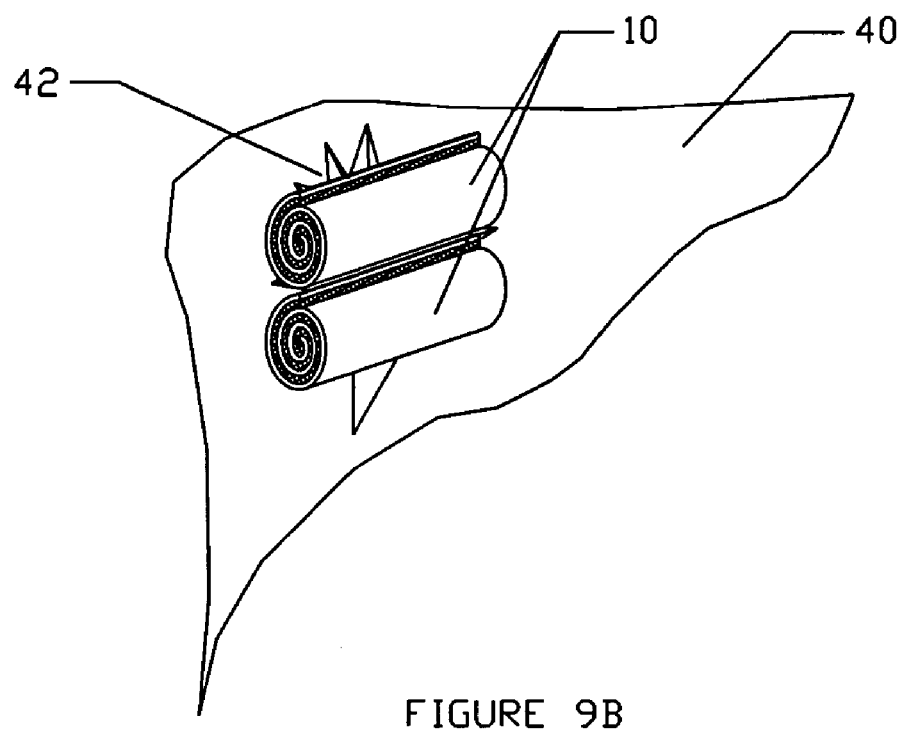
FIG. 9B illustrates the wound of the liver being treated by application of internal tamponade of hemorrhage with the impermeable hemostatic packing device used in a perihepatic location, according to aspects of the invention.

FIG. 9B illustrates the wound 42 to the liver 40 being treated by application of intra-parenchymal packing using one or more hemostatic packing devices 10. In this embodiment, two hemostatic packing devices 10 are used to provide hemostasis for the wound 42. The hemostatic packing devices 10 are applied manually via open surgery, in this case.

Figure 10A:
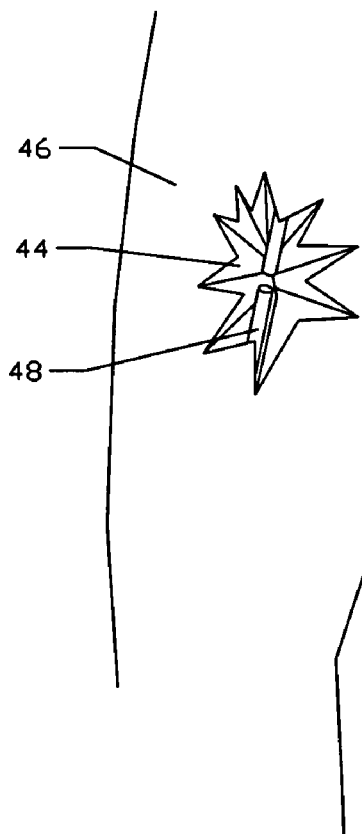
FIG. 10A illustrates a wound of an exemplary extremity, the thigh, with femoral artery transection, according to aspects of the invention.

FIG. 10A illustrates a wound 44 to the periphery and more specifically, the thigh 46. The wound 44 has caused femoral artery 48 to become transected.

Figure 10B:
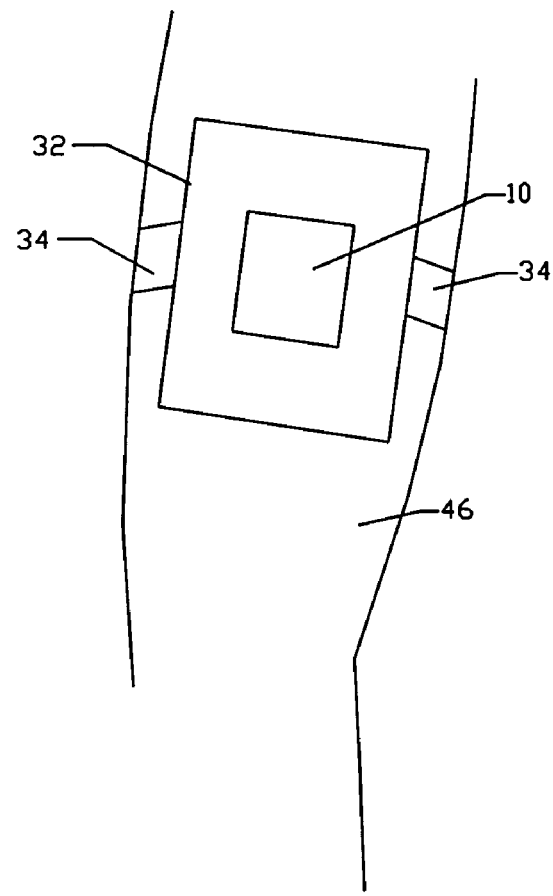
FIG. 10B illustrates the wound to the thigh being treated by application of an impermeable hemostatic packing device with the adhesive impermeable drape, according to aspects of the invention.

FIG. 10B illustrates the wound 44 to the thigh 46 being treated by application of the impermeable hemostatic packing device 10 with an adhesive impermeable drape 32 and straps 34.

In yet another embodiment, a wound closure device is fabricated from a material that has skin and wound contact surfaces that are impermeable to water, blood and tissue penetration. Preferably, these wound closure devices are fabricated from sheets of materials such as, but not limited to, polyurethane, polypropylene, polyethylene, silicone elastomer, and the like. The skin contact surface is a biocompatible adhesive and is further impregnated with anti-microbial agents such as, but not limited to, iodine, betadine and the like. The bandage, peripheral hemostasis wrap (PHW), or wound closure device is large enough to completely surround the wound and seal in the wound so that blood cannot escape. The bandage, optionally, has additional straps that fully surround the body or appendage and seal with Velcro, buckles, clamps or the like. The straps may be fabric or they may be rubberized or coated, fluid impermeable fabric, or they may be sheets of polymer. The bandage or wound closure device seals the wound against the full systolic blood pressure and, thus tamponade any bleeding that occurs from damaged vessels other than the one repaired with the shunt 10. The bandage comprises an adhesive region that sticks to the skin, even if the skin is wet or bloody. The bandage, or peripheral hemostasis wrap, is optionally maintained in place using straps that wrap around the body or appendage and secure the bandage in place with adequate pressure to generate pressure tamponade of the wound. Adhesive methodologies will suffice to hold the bandage in place in many cases. However, non-adhesive methodologies such as hook and loop fasteners or buckles will work in almost all applications. The straps 34, in a preferred embodiment, are fabricated from materials that have longitudinal or axial stretch. Stretching of the straps 34 in the lateral direction is not preferable. Flexibility in both the lateral and longitudinal directions is preferable for the straps 34. In a preferred embodiment, the straps 34 with latching devices provide the only form of attachment of the wound closure device to the patient. The straps 34, in one embodiment, are wrapped one or more times over the liquid impermeable region of the bandage to provide for extra tightness and control of pressure. The straps 34 are configured to exert sufficient force on the fluid impermeable bandage to seal the packing device into the wound or any dams or gaskets against the skin in order to prevent or minimize blood loss from the wound. The straps 34 are further configured to distribute pressure on the body so that a tourniquet effect does not occur and so that blood flow is not impeded in any area except the wound itself. The straps 34 distribute pressure by maintaining a wide footprint and not kinking so as to form a small width high-tension area, which could be a problem. For short-term applications, the need for tissue impermeability is less important than the need for liquid (e.g. blood and water) impermeability. A scrim, not shown, is also useful to back up the fluid impermeable region 32 and prevent stretching or distortion of the fluid impermeable drape or region 32. Further, the straps 34 may be fabricated as a rigid or semi-rigid shell or cuirass to prevent a tourniquet effect from occurring on the limb being treated. A tourniquet effect is that result when a tight band or cord is wrapped around a limb, thus preventing or restricting arterial blood flow, venous return blood flow, or both.

The preferred wound closure is a large piece of Ioban, a trademark and product of 3M Corporation, the non-adhesive side of which is adhered to a piece of woven gauze or mesh to provide adequate structure to the weak membrane of the Ioban. The Ioban has adhesive and anti-microbial properties preferred for this application. A strap extending from opposing ends of the bandage and terminated with Velcro or 3M Coban, which is self-adherent, assists in maintaining pressure against the wound and proving full tamponade of the hemorrhage. In yet a further embodiment, the central part of the skin contact region comprises a malleable or conformable pad, preferably adhered to the wound closure device, which helps to exert hemostatic force on the wound. The conformable pad evenly distributes the forces throughout the wound so that no areas receive either too high a pressure, or too low a pressure, such as would permit further bleeding. The conformable central pad may be a block of foam covered by the aforementioned impermeable layer, or it may be an impermeable membrane, preferably elastomeric, filled with liquid such as saline or even a particulate material such as, but not limited to, sand, flour, sugar, silicone oil, or the like. In a preferred embodiment, the material used to form the fluid-tight membrane is liquid impermeable but gas permeable. Materials suitable for such permeability requirements include expanded polytetrafluoroethylene (ePTFE) and the like.

Figure 11:
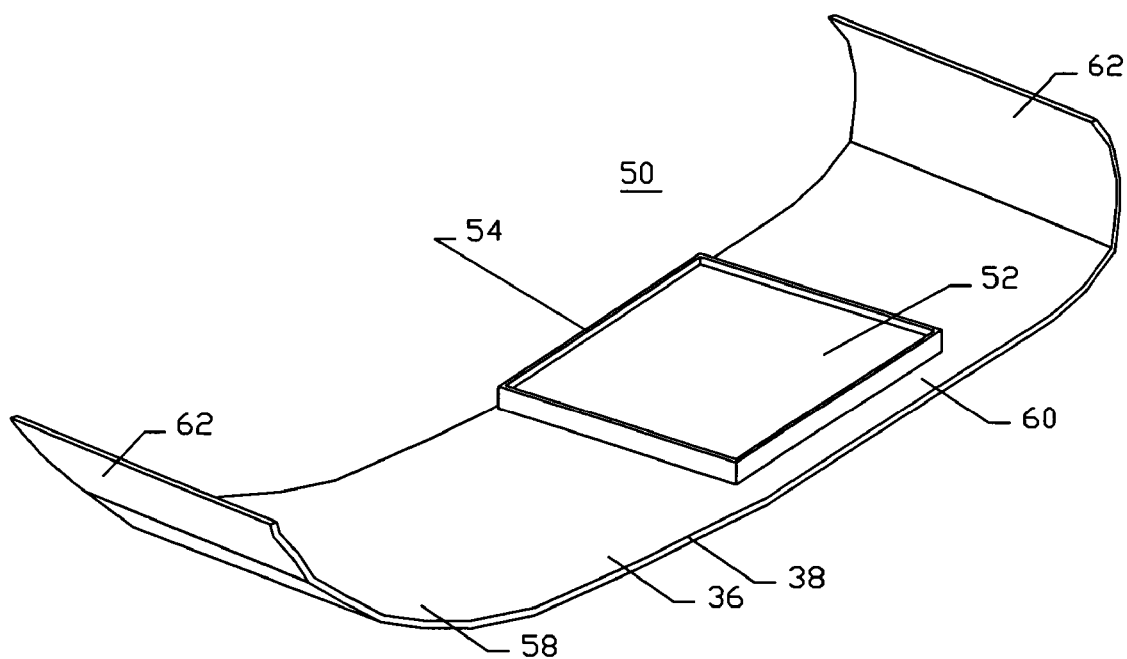
FIG. 11 illustrates a wound dressing, PHS, or bandage for treating a wound to the arm or the leg comprising a blood dam, according to aspects of the invention.

FIG. 11 illustrates another embodiment of the present invention. The hemostatic packing device 10 is in the form of a wound dressing, PHS, or bandage 50. The wound dressing, PHW, or bandage 50 further comprises an optional gauze or absorbent region 52. The gauze or absorbent region 52 may have material bulked up or rolled up to aid in the application of pressure to cause pressure tamponade of the wound or perforation to the body. The gauze or absorbent region 52 may alternatively be a fluid pouch, which may be inflated or deflated to apply the required pressure tamponade to the wound area. The gauze or absorbent region 52 is further comprised of a peripheral gasket 54 or a plurality of gaskets 54 running in a honeycomb, rectangular, nested oval, nested rectangle, concentric ring, concentric oval, concentric rectangle, or other appropriate pattern throughout and within the gauze or absorbent region 52 of the bandage 50. The gauze or absorbent region 52 preferably further comprises a fluid or liquid impermeable barrier that prevents the escape of blood from the wound area, even under systemic systolic arterial pressure. The gasket 54 is sealed to the fluid or liquid impermeable barrier to prevent the escape of blood out the side of the bandage at pressures up to that of systemic systolic arterial pressure.

The gasket 54 aids in hemodynamic control and is made out of fluid impermeable, elastomeric or compliant materials, such as, but not limited to, silicone, C-flex, hydrogels, silicone oil-filled membrane, polyurethane closed-cell foam, and the like. The typical width of the gasket 54 material will be ⅛ to ¼ inch. However, it should not be limited to these dimensions, as there may be wounds that require greater hemodynamic stabilization using the here claimed damming concept or technique. The gasket 54 is wide enough to distribute pressure over the skin area so as not to cause petcheciae, bruising or tissue damage but enough pressure to seal against systemic arterial pressure, typically 100 to 300 mm Hg. The absence of petcheciae is preferable but is not essential for performance of the gasket 54. The gasket 54 should press into the skin hard enough to form a complete liquid-impermeable seal. Bruising of the skin is generally considered to be an acceptable alternative to bleeding to death. The dam or gasket 54 generally presses gently into the tissue surrounding the wound to ensure a strong resistance to hemorrhage or leakage of blood beyond the dam. The gasket 54 or dam is configured to indent the skin and seal against the skin so as to prevent the loss of blood at systolic systemic blood pressure levels. The gasket 54 or dam is configured with a skin contact surface that has a cross-section that includes, but is not limited to, triangular, rounded, trapezoidal, rectangular, rounded triangular, and the like. The gasket 54 or dam further is configured without any bumps, defects, or gaps that wound permit liquid loss between the gasket 54 and the skin when pressed together. The gasket 54 to skin contact and seal is generally improved by the presence of water, blood, or other liquids. In one embodiment, a fluid impermeable region exists in the area inside the gasket 54.

Affixed or integral to the gauze or absorbent region 52 is a plurality of optionally fluid impermeable straps 58 that will wrap around the extremity or wound area. The straps 58 may contain an adhesive layer 36 or may be of material suitable for stretch wrapping, or they preferably comprise mechanical fasteners. Optionally, the straps 58 may comprise an adhesive layer 36 and a backing layer 38. The backing 38 is, preferably, fabricated from non-elastomeric materials such as, but not limited to, polyethylene, polypropylene, Tyvek, polytetrafluoroethylene, polyester, and the like. Another option for the straps 58 could be self-adhesive straps 58 made from materials such as, but not limited to, those manufactured by 3M, Inc., under the trade name of Coban. This material would be suitable and desirable for use as the straps 58 due to its chemical composition and inherent antiseptic properties. In addition, the wrapping material may also have buckles or hook and loop fasteners such as Velcro 62 or another means of securing or attaching the bandage in place on the patient. Self-adhesive materials such as, but not limited to, those manufactured by 3M, Inc., under the trade name of Coban are suitable for use as the binding system for the straps 58. The straps 58 may also be fluid impermeable and optionally possess at least some degree of elastomeric properties, so as to aid in the wound containment. The bandage or wound dressing 50 also has a free end or side 60. Ideally, the wound dressing or bandage 50 would be packaged with a protective, removable layer over the gauze or absorbent region 52 and quite possibly over the entire surface applied to the patient.

The straps 58, in a preferred embodiment, comprise elements, which are elastomeric in the longitudinal direction. The elastomeric members in the straps 58 make it easier to apply the bandage and facilitate wrapping the straps 58 tightly enough that the bandage is able to seal against systemic arterial pressure. It is preferable to size the straps 58 to permit the straps to be wrapped around the limb or body part a plurality of times so as to hold the liquid impermeable region and any dams or gaskets tightly over the wound. The straps 58, in one embodiment, are non-elastomeric or have non-stretching elements affixed thereto in a region encompassing at least the fluid impermeable region. The non-elastomeric or non-stretchable region is generally non-deformable except in flexion. The straps 58 are sized to fit the body part being treated. The width of the straps 58 ranges from ½ inch or less to over 36 inches. Preferably the width of the straps 58 ranges from ½ inch to 12 inches. The length of the strap 58 is sized to allow for at least one wrap around the body part, and preferably, a plurality of wraps.

Figure 12:
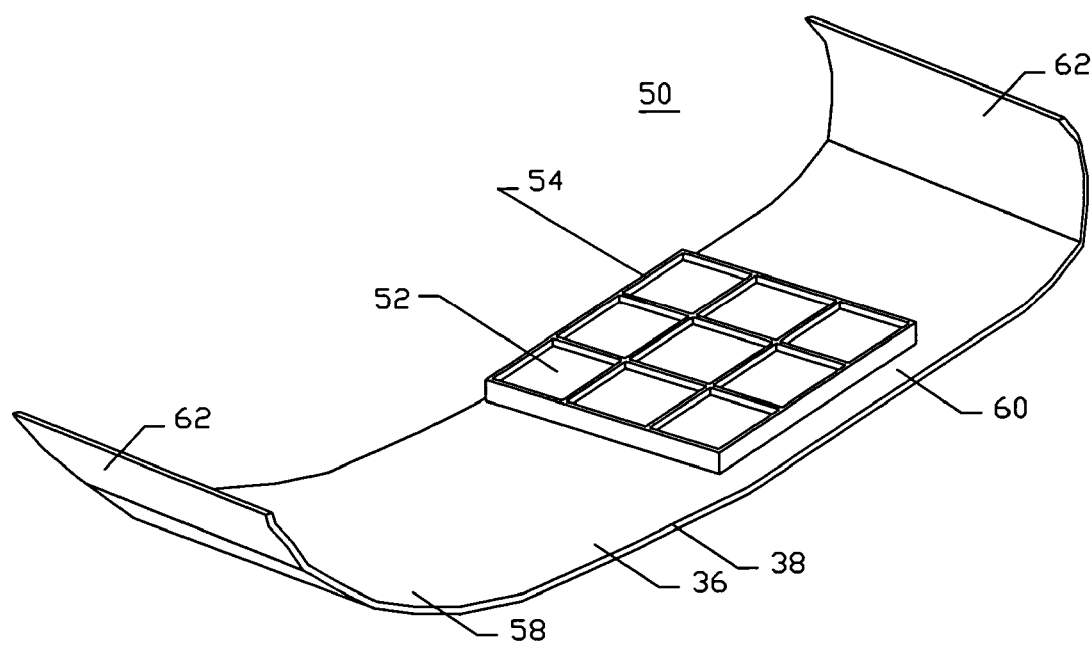
FIG. 12 illustrates a wound dressing, PHS, or bandage for treating a wound to the arm or the leg comprising a series of blood dams, according to aspects of the invention.

FIG. 12 illustrates another embodiment of the present invention. The hemostatic packing device 10 is in the form of a wound dressing or bandage 50, as shown in FIG. 11. The wound dressing or bandage 50 further comprises a gauze or absorbent region 52. The gauze or absorbent region 52 is generally a central region in the bandage that covers the wound. This region 52 in another embodiment, may not be absorbent or gauze covered at all, but merely a liquid impermeable central wound covering region. The gauze or absorbent region 52 is further comprised of a plurality of dams or gaskets 54 running or weaving in a honeycomb, rectangular, diamond, or other appropriate pattern throughout and within the gauze or absorbent region 52 of the bandage 50. The gasket 54 aids in hemodynamic control and is made out of fluid impermeable materials, such as, but not limited to, silicone, C-flex, hydrogels, silicone oil-filled membrane, polyurethane closed-cell foam, and the like. The typical width of the gasket 54 material will be ⅛ to ¼ inch. However, it should not be limited to these dimensions, as there may be wounds that require greater hemodynamic stabilization using the here claimed damming concept or technique. The gasket 54 is wide enough to distribute pressure over the skin area so as not to cause petcheciae, bruising or tissue damage but enough pressure to seal against systemic arterial pressure, typically 100 to 300 mm Hg. The gasket or dam 54, in one embodiment, does cause bruising or petcheciae of the skin. The presence of petcheciae, while not optimal, does not detract from the performance of the gasket 54 and is generally considered to be an acceptable alternative to bleeding to death. The dam or gasket 54 further comprises a tissue contacting edge that is configured with a rounded, rectangular, triangular, trapezoidal, rounded triangular or other shaped cross-section. The dam or gasket 54 is pressed against the skin with enough force to prevent the escape of blood under systemic arterial pressures, which can range from 80 mm Hg to over 200 mm Hg. The dam or gasket 54 seals to the liquid impermeable covering of the bandage by being integrally formed, by adhesives, by overmolding, by heat welding, by ultrasonic welding, or other process. The dam or gasket 54 does not seal to the skin by adhesives. The use of adhesives in the dam or gasket 54 would be of little value since the bandage would be placed on a wound in an acute setting, which is often, wet, bloody, oily, dirty, or all of the above. In such environments, there are very few, if any, adhesives that could hold a seal to the skin and prevent the escape of blood under systemic arterial pressure.

Figure 13:
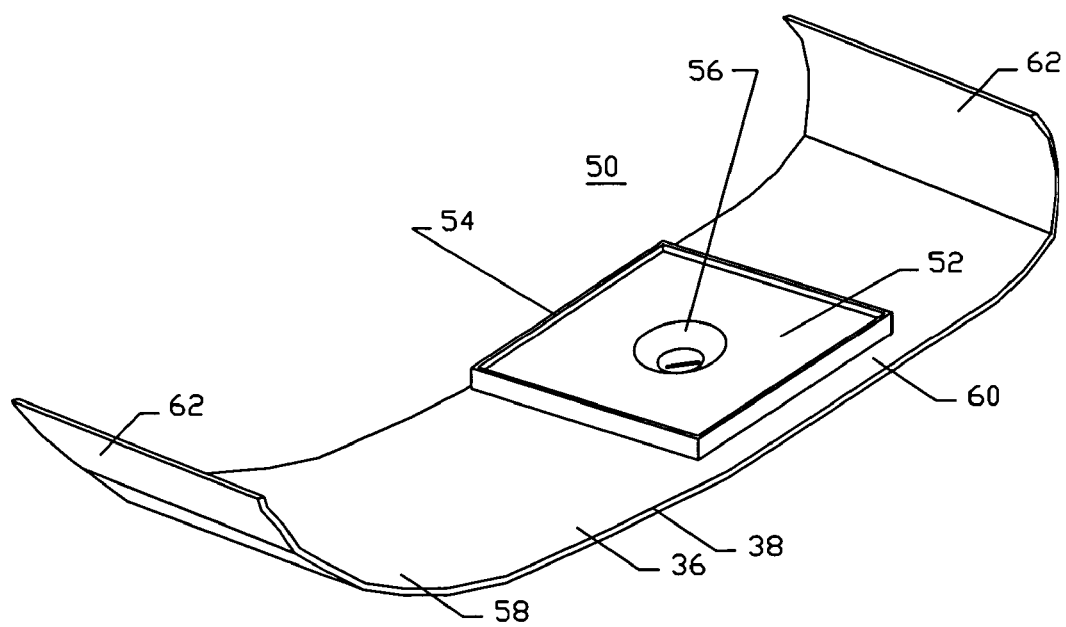
FIG. 13 illustrates a wound dressing, PHS, or bandage for treating a wound to the arm or the leg comprising a blood dam with a communicating valve, according to aspects of the invention.

FIG. 13 illustrates another embodiment of the present invention. The hemostatic packing device 10 is in the form of a wound dressing or bandage 50, as shown in FIG. 11. The wound dressing or bandage 50 further comprises a gauze or absorbent region 52 and a valve 56. The valve 56, which resides within the gasket 54, may be used to remove fluids or add agents to assist in the coagulation or wound containment. The valve 56 may be, but is not limited to, a duck bill type of valve, stopcock, or the like.

Figure 14A:
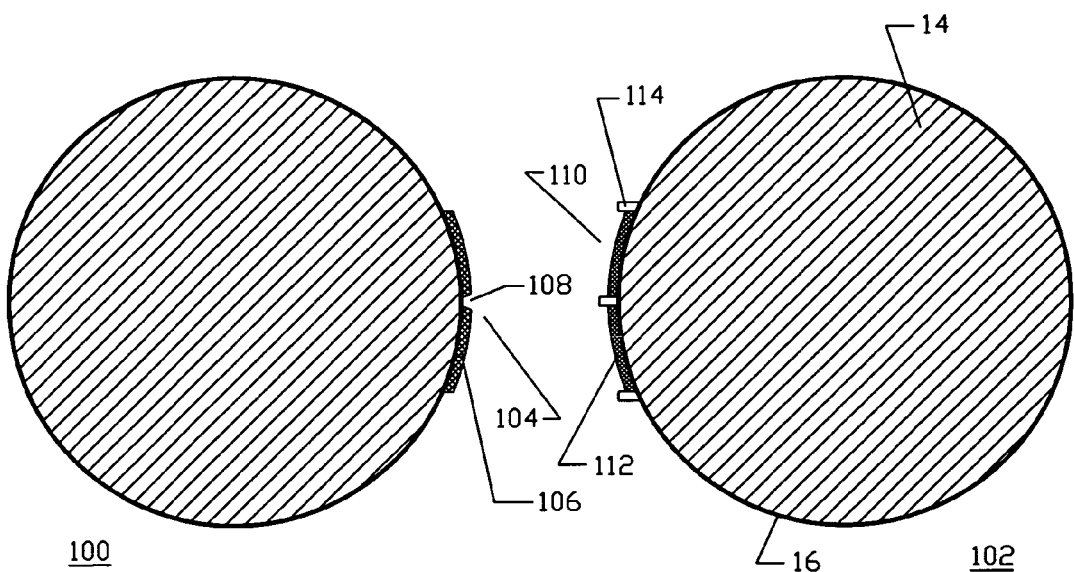
FIG. 14A illustrates a lateral sectional view of two internal hemostatic packs for solid organs, viscera, and the like, comprising an adherent region for joining the two packs, wherein the adherent region comprises a porous adhesive element but further comprises a plurality of non-porous barrier regions or dams, according to aspects of the invention.

FIG. 14A illustrates a cross-sectional view of another embodiment of two internal packs 100 and 102 comprising an impermeable outer layer 16 and a soft-conformable filler region 14. The left hand internal pack 100 further comprises a female adhesive region 104 further comprising an adhesive material 106 and a plurality of adhesive material gaps 108. The right hand internal pack 102 further comprises a male adhesive region 110 further comprising an adhesive material 112 and a plurality of dams 114.

Referring to FIG. 14A, the left hand internal pack 100 and the right hand internal pack 102, in the preferred embodiment each has at least one male adhesive region 110 and one female adhesive region 104 so that a plurality of packs can be chained together to form a contiguous blood impermeable barrier. In the preferred embodiment, the adhesive material 106 is the hook style of Velcro fastener while the adhesive material 112 is the tufted style of Velcro fastener. Thus when the adhesive regions 106 and 112 are brought into contact, they adhere to each other. The adhesive regions 106 and 112 are reversibly adherent to each other and may be separated by manual force, if desired. In another embodiment, the adhesive regions 106 and 112 may be fabricated from materials such as, but not limited to, 3M Coban and the like, hydrogel adhesives and the like, and typical adhesives such as are used in medical bandages. The adhesive material gaps 108, in the female adhesive region 104 are spaced and designed so that the dams 114 of the male adhesive region impinge on and seal against an impermeable surface of the female adhesive region 104. The adhesive material gaps 108 and the dams 114 may be configured in a straight line or they may be curved into a wavy pattern to improve the sealing area. Special guide markers either printed on the packs 100 and 102 or fabricated as raised or detented surfaces on the packs 100 and 102 facilitate alignment of the dams 114 and the adhesive material gaps 108.

Figure 14B:
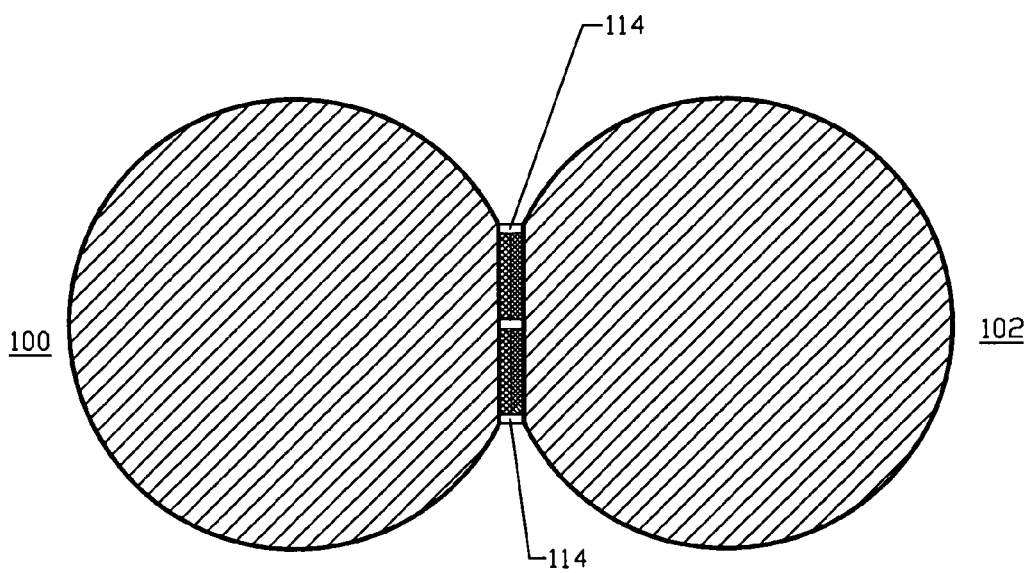
FIG. 14B illustrates a lateral sectional view of two internal hemostatic packs that have been joined together to form a syncytium wherein the barrier regions or dams render the adherent region impermeable to fluids such as blood, according to aspects of the invention.

FIG. 14B illustrates a cross-sectional view of the internal packs 100 and 102 following joining to form a continuous barrier pack. Referring to FIGS. 14A and 14B, the dams 114 seal against the impermeable surface 16 through adhesive material gaps 108. The adhesive regions 106 and 112 are firmly in contact and grip each other to hold the two packs 100 and 102 together without any area of seepage, leakage, or weeping.

In yet another embodiment of the barrier pack, the mating region between the two packs comprises adhesive regions such as those described for FIG. 14A, except that the barrier dams are replaced with fluid impermeable flaps that fold in to cover the adhesive regions following joining. One flap preferably covers each side of the adhesive region. In a preferred embodiment, the flaps cover the adhesive regions until they are needed to join with another barrier pack. At that time, the flap is pulled away, the two packs are joined, and the flap is folded in to cover the adhesive region and form a fluid-tight seal between the two barrier packs.

Referring to FIG. 1 through FIGS. 14A and 14B, the hemostatic packing device 10 is used to treat wounds that are typically caused by trauma. In a typical procedure, the surgeon or medic, using aseptic procedure, accesses the wound either by open surgery or laparoscopic surgery. The wound is irrigated and cleaned and excess fluids are removed by suction and blotting with gauze sponges. The surgeon may apply antiseptic agents or thrombogenic agents to the wound. The surgeon places the hemostatic packing device 10 into the wound and the device 10 is secured into place. Using current damage control procedure, it is preferable to stabilize the patient prior to removing the hemostatic packing device 10 and permanently repairing the wound.

The hemostatic packing device 10 does not stick or heal into the wound and removal is not traumatic to the patient. The hemostatic packing device further does not introduce contaminants or debris, a problem with prior art, powdered hemostatic agents, which would be difficult to remove to perform definitive repair and which would increase the likelihood and severity of wound infection. Referring to FIG. 13, he hemostatic packing device 10 is also well suited for a typical "sucking chest wound" because of its inherent impermeable properties. The one-way valve 56 permits fluid and air to exit the chest cavity but prohibits reflux of air into the chest cavity, a condition which prevents lung function and which is known as pneumothorax.

Figure 15:
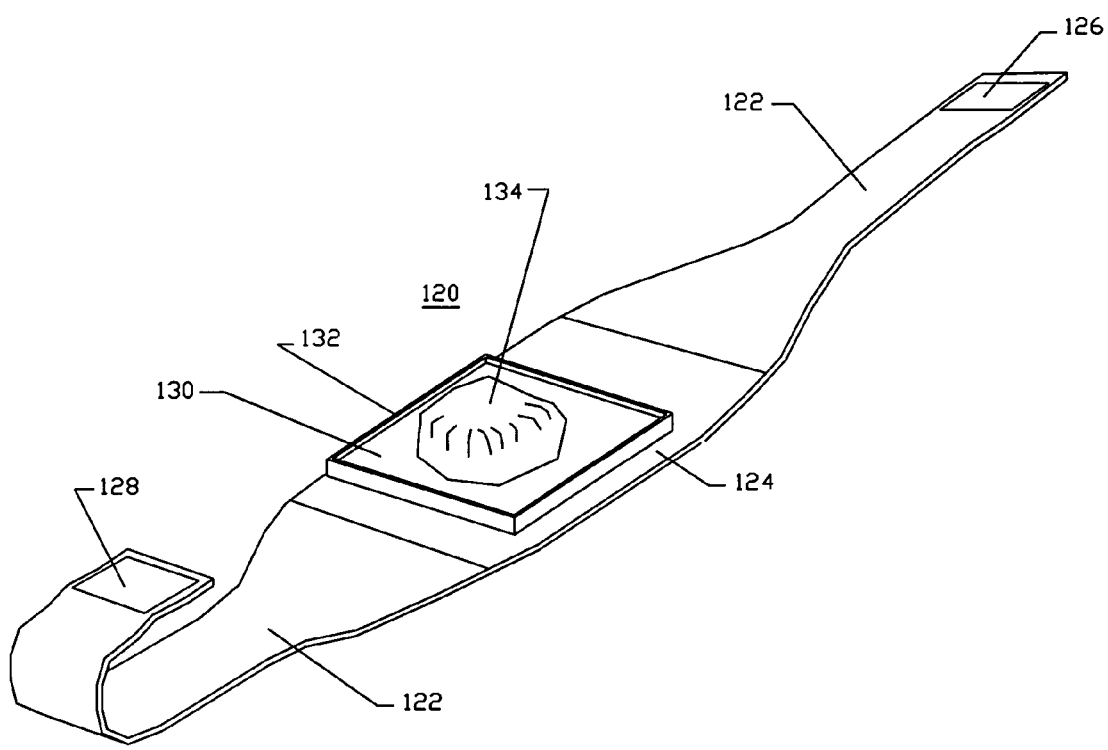
FIG. 15 illustrates an oblique view of a preferred wound dressing, PHS, or bandage for treating a wound to a body part comprising a strap, a blood dam, and a pillow pack, according to aspects of the invention.

FIG. 15 illustrates a preferred embodiment of a wound dressing or bandage 120. The wound dressing or bandage 120 comprises a backbone 122 with a central region and two ends, a first fastener 126, a second fastener 128, a fluid-impermeable barrier 124, a fluid dam 132, a pillow pack 134, and an optional peripheral hemostatic region 130.

Referring to FIG. 15, the wound dressing or bandage 120 is configured to wrap around a body part, arm, leg, torso, head, etc. and fasten using the first fastener 126 and the second fastener 128. The bandage 120 is pre-packaged in a barrier package that prohibits contamination. Following packaging, the bandage 120 and package are sterilized using ethylene oxide, gamma radiation, E-beam radiation, or the like. In a preferred embodiment, the package comprises an inner and an outer pouch which are sealed and which constitute a double-aseptic package. The fasteners 126 and 128 are of the type including, but not limited to, Velcro, buckles, snaps, jam cleats, buttons, and the like. Fastener 128 is, in a preferred embodiment, a loop fastener, while fastener 126 is the hook fastener. In another embodiment, there are a plurality of loop fasteners 128 or a continuous loop fastener along a large region of the bandage 120. In another embodiment, a plurality of hook fasteners 126 are comprised by the bandage 120. In a preferred embodiment, the hook fastener 126 is affixed at one end and on one side of the backbone 122. The fluid impermeable region and gaskets are affixed to the same side of the backbone 122 as the hook fasteners 126. The side of the backbone 122 opposite that of the hook fasteners 126 comprises loop structures, such as those found in Velcro loops, covering essentially the entire side, that compatibly lock or reversibly engage with the hook fastener 126. This configuration is preferable because it permits a wide range of adjustability in locking the bandage in place. Other conceivable lock structures are appropriate in this application. An optional cinch mechanism to increase mechanical advantage and allow the caregiver to apply the PHS or bandage 120 with increased compression may be added to the configuration. The backbone 122 is preferably a woven or knitted fabric of material such as, but not limited to cotton, polyester, polypropylene, polyurethane, polyethylene, PTFE, nylon, and the like. The woven backbone is configured to be flexible but have high tensile strength, while porosity is not an important characteristic. The impermeable barrier 124 is preferably applied to the central region of the bandage 120 and is created by a separate polymer layer that is adhered or welded to the backbone 122. The backbone 122 may also be dipped, sprayed, or coated with materials such as, but not limited to, polyurethane, C-Flex thermoplastic, silicone elastomer, and the like. Since the dressing is intended for short-term application, gas permeability is not considered objectionable but it is desirable. The fluid dam 132 is fabricated from materials including those used to fabricate the fluid impermeable barrier 124. The fluid dam 132 may also be fabricated from gel-filled membranes, hydrogels, oil-filled membranes, and the like. The membrane of the fluid dam 132 is preferably, inelastic at the pressures used for filling. The fluid dam 132 is configured to provide a pressure seal against the body and form a complete barrier to prevent blood from escaping the wound. In another embodiment, the fluid dam 132 is inflatable following or before application to the patient through a valve such as a stopcock or standard inflation valve on the exterior surface of the bandage 120.

Further referring to FIG. 15, the pillow pack 134 is adhered to the central region of the bandage 120, preferably adhered to the fluid impermeable region 124. The pillow pack 134, preferably resides within the region described by the fluid dam 132. The pillow pack 134 outer surface is preferably smooth and resistant to blood adherence but in another embodiment, the pillow pack 134 outer surface may be a fabric mesh or other convoluted surface capable of accelerating thrombosis or of carrying thrombogenic materials or antimicrobial agents. The thrombogenic materials are preferably spreadable gels or liquids. Typical thrombogenic materials include fibrin, substances that remove water from blood and cause coagulation, or other materials derived, for example from crustaceans, and which exhibit thrombogenic properties when exposed to blood. The pillow pack 134 is the primary distributor of force upon the wound to generate pressure tamponade. The pillow pack 134 is capable of extruding into a wound and distributing pressure evenly to generate hemostasis. The pillow pack 134 preferably comprises an elastomeric membrane filled with materials such as, but not limited to, air, water, oil, sand, gel materials, and the like. The pillow pack 134 in the embodiment where gas, air or liquid, is used for inflation, comprises an optional valve such as stopcock on the exterior surface of the bandage 120. The peripheral hemostasis region 130 preferably resides within the fluid dam 132 and accelerates clotting in the region outside the wound area but within the environs of the bandage 120. In a preferred embodiment, the peripheral hemostasis region 130 comprises materials, which are elastomeric thus allowing the pillow pack 134 to apply a predetermined or known amount of force to the wound. The peripheral hemostasis region 130 is fabricated from materials such as, but not limited to, cotton gauze, polyester knits and the like.

Figure 16:
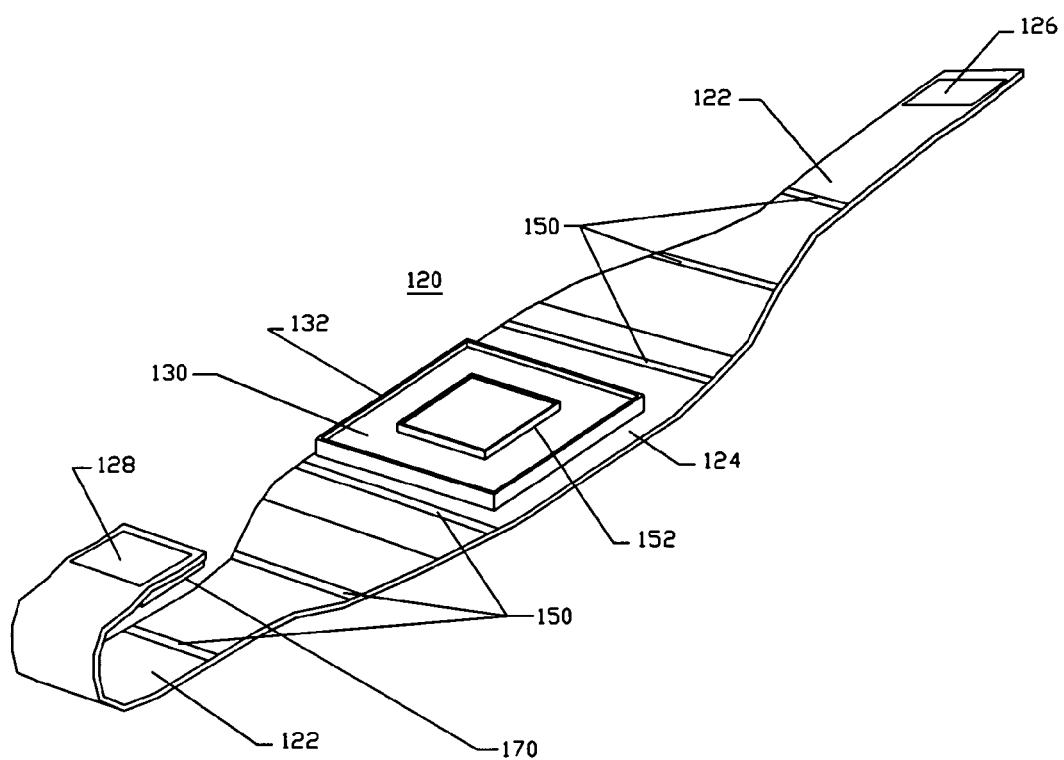
FIG. 16 illustrates an oblique view of a wound dressing, PHS, or bandage for treating a wound to a body part comprising a strap, a plurality of concentric blood dams, lateral stiffeners and a liquid impermeable central region, according to aspects of the invention.

FIG. 16 illustrates another embodiment of a wound dressing or bandage 120. The wound dressing or bandage 120 comprises a backbone 122 with a central region and two ends, a first fastener 126, a second fastener 128, a fluid-impermeable barrier 124, an outer fluid dam 132, an inner fluid dam 152, an optional pillow pack 134, an optional peripheral hemostatic region 130, an optional adhesive region 170, and a plurality of lateral stiffeners 150.

Referring to FIG. 16, the backbone 122 provides the structure to which other components are affixed. The fluid impermeable barrier 124 is permanently affixed near the central portion of the backbone 122 and is sized to completely cover a wound. The fluid impermeable barrier 124 is affixed to the backbone 122 with adhesives, heat welding, mechanical interlocks, or the like. The lateral stiffeners 150 are affixed to the backbone and prevent lateral collapse or wrinkling of the backbone. The lateral stiffeners 150 possess column strength and they are flexible. The lateral stiffeners 150 may optionally be elastomeric or stretch beyond their unstressed configuration but they cannot be substantially compressed below their unstressed configuration. The lateral stiffeners 150 may be discrete elements, like sail battens, or they may be a sheet of material integral to or attached to the backbone 122. The backbone material 122 is preferably permeable to gas or even liquids, however the central fluid impermeable barrier 124 is not permeable to liquids such as blood, water, oil, or the like. In one embodiment, the backbone material 122, in the region of the fluid impermeable barrier 124 is preferably, not elastomeric in either the longitudinal or the lateral direction.

The inner dam 152 and the outer dam 132 are permanently affixed to the backbone 122 so that only fluid impermeable barrier exists on the interior of the outer dam 132. The multiplicity of dams 132 and 152 allows greater flexibility in sizing the bandage because only one of the dams needs to provide the seal against systemic arterial pressure. The exact number of dams is undetermined and could range from one to 50 or more. Practically, the number of dams will be in the range of 1 to 10. The dams form a nested pattern of rings that may be ovals, squares, circles, or the like. The dams have a skin contact surface that is even and smooth with no distortion or gaps. The dams have structure to resist gross distortion but elastomeric enough to cushion the skin when pressed thereon. In another embodiment, an asymmetrical tightening mechanism is provided which allows for relative tightening of one side of the PHS or bandage 120 relative to the other. The asymmetrical tightening mechanism is advantageous, when placing the bandage 120 on a tapered body member such as a forearm or thigh, to obtain even pressure distribution on the dams 132 or 152 or both. The asymmetrical tightening mechanism can also be useful to cinch the bandage so that observed hemorrhage from beyond the dams 132 and 152 are substantially eliminated.

The optional adhesive region 170 is affixed to the same side of the PHS or bandage 120 as is the dam 132. The adhesive region 170 is located adjacent to but outside the dam 132. The adhesive region 170 is preferably affixed to the PHS or bandage 170 at or near an end. The adhesive region 170 serves to allow for initial placement and stabilization of one end of the bandage 120 against the patient's body so that the PHS or bandage 120 can be wrapped with one hand. The adhesive region 170 also allows for generation of correct tension when wrapping the bandage 120 around the body part or limb. In a preferred embodiment, the outer dam 132 is affixed to the backbone 122 relatively closer to the end of the bandage 120 where the adhesive region 170 is located than to the other end of the bandage 120. Thus, in this preferred embodiment, the dams 132 and 152 are located closer to one end of the bandage 120 than to the other end. The adhesive region 170 is preferably fabricated from adhesives that work in a wet or bloody environment. Such adhesives, while not extremely strong, offer sufficient adherence to stabilize the bandage for initial wrapping. Hydrophilic hydrogels and other materials known in the art comprise materials suitable for fabrication of a wet-adhesive region. The fastener 128 in a preferred embodiment is the loop of a hook and loop fastener while the fastener 126 is the hook of the hook and loop fastener. In another embodiment, the adhesive region 170 is replaced or augmented by an elastomeric ring or wrap (not shown) through which the limb is placed. The ring or wrap is affixed to the backbone 122 at the same end of the bandage 120 as the adhesive region 170 and temporarily secures the bandage 120 to the limb until the backbone 122 can be wrapped securely around the limb or body part.

Figure 17A:
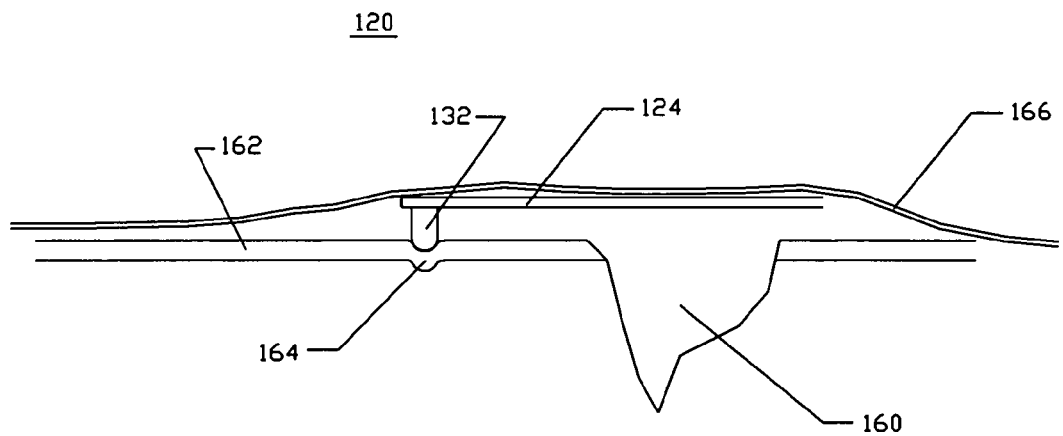
FIG. 17A illustrates a side cross-sectional view of a wound with a bandage or PHS comprising a liquid impermeable region surrounded by a dam or gasket wherein the dam or gasket edge is rounded and is pressed into the skin surrounding the wound, according to aspects of the invention.

FIG. 17A illustrates a wound 160 covered by a hemostatic bandage 120 or PHS further comprising a liquid impermeable region 124, a strap 166, and a dam 132. The wound is surrounded by a layer of skin 162 with a dimpled region 164. The strap 166 is of sufficient tightness to hold the dam 132 against and pressing into the skin 162 to form a dimple 164 and a barrier against pressurized blood. Blood cannot escape the environs of the PHS or bandage 120. The strap 166 is configured with elastomeric elements in the longitudinal direction to facilitate generation and control of sufficient tensile forces to cause hemostasis. The elastomeric elements are fabricated from material such as, but not limited to polyurethane, Lycra, silicone elastomer, thermoplastic elastomer, and the like. The fabric of the strap 166 may be porous or may be rubberized or sealed against fluid escape. Elastomeric properties can also be achieved by fabric forming processes such as, but not limited to, weaving, knitting, crocheting, and the like. In another embodiment, mechanical elements are provided to tighten the bandage straps 166 in a controlled fashion. The mechanical tightening elements include winches, pulleys, turnbuckles, levers, inflatable elements such as bladders, and the like. A plurality of such tightening elements, in one embodiment, are distributed so as to permit selective or controlled tightening of one or both edges of the straps 166. The dam 132 has a skin 162 contact surface that is rounded so as to be minimally traumatic causing temporary dimpling 164.

Figure 17B:
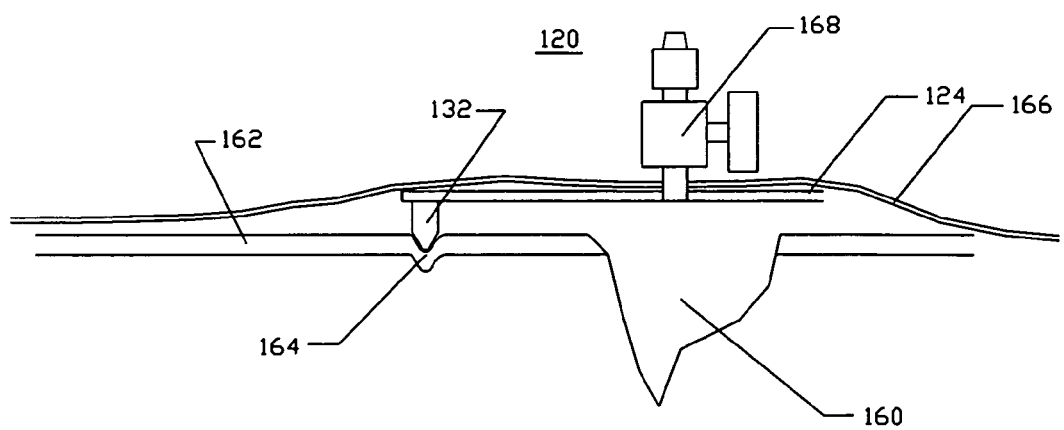
FIG. 17B illustrates a side cross-sectional view of a wound with a bandage or PHS comprising a fluid access port and valve and a liquid impermeable region surrounded by a dam or gasket wherein the gasket has a rounded triangular cross-section, according to aspects of the invention.

FIG. 17B illustrates a wound 160 surrounded by a layer of skin 162, covered by a hemostatic bandage 120 further comprising a liquid impermeable region 124, a strap 166, a dam 132, and a fluid port and valve 168. The fluid port and valve 168 are affixed to the fluid impermeable region 124 and permit liquids or gasses to be injected or removed from the space between the liquid impermeable region 124, the dam 132, the wound 160 and the skin 162. Injection of liquids such as saline or water or even gasses may be advantageous in causing distributed pressure within the wound 160 to cause hemostasis against restricted or unrestricted systemic arterial pressure. Such fluid injected into the wound region under the liquid impermeable region 124 is preferably pressurized to a level exceeding systemic systolic arterial pressure, typically in the range of 100 mm Hg to 250 mm Hg, depending on the level of hypertension of the individual. The dam 132 has a skin contact surface that is triangular in cross section with a slight rounding to minimize trauma to the skin 162. The dimple 164 is formed in the skin by the pressure applied to the dam 132. The liquid impermeable region 124 is held against the skin 162 by the strap or straps 166 and fastened with fasteners that work in a wet, contaminated environment.

Figure 18:
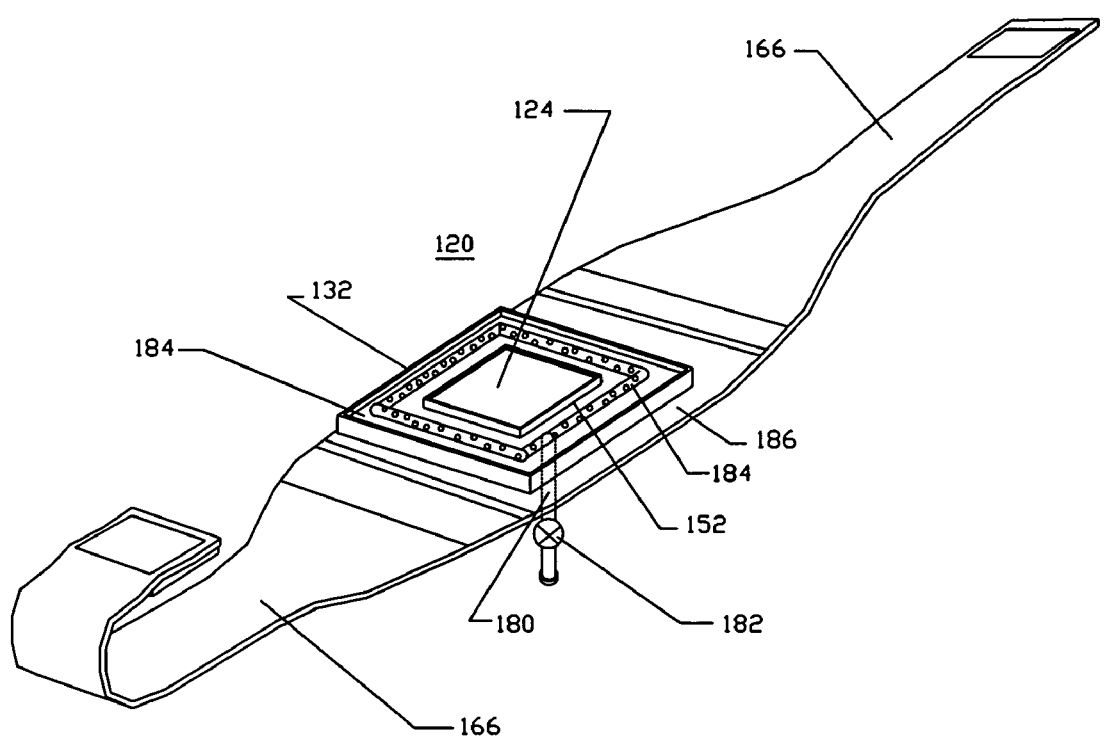
FIG. 18 illustrates an oblique view of a wound dressing, PHS, or bandage for treating a wound to a body part comprising an optional strap, a plurality of nested blood dams, a stiffening scrim, a central liquid impermeable region, a vacuum port, and vacuum manifold, according to aspects of the invention.

FIG. 18 illustrates yet another embodiment of the bandage 120 wherein it is held against the skin surrounding a wound by a vacuum. In this embodiment, the bandage 120 comprises a liquid impermeable region 124, an inner dam 152, an outer dam 132, a vacuum port 180, a vacuum valve 182, a vacuum manifold 184, a scrim 186, and an optional strap 166. The fluid port 180 and valve 182 are used to facilitate pulling a vacuum under the liquid impermeable region 124 of the bandage 120 to hold the bandage 120 in place. A pump to continuously draw a vacuum is preferable to a pump that is deactivated after the vacuum is created, because of leakage of the vacuum at the seals could occur, resulting in hemorrhage from the wound 160, unless the vacuum loss is corrected. The scrim 186 is affixed to the liquid impermeable region 124 so as to permit flexion but not stretch of the liquid impermeable region 124. The scrim 186 may further be extended to provide additional reduction in stretch characteristics of the strap 166, which is generally elastic in nature.

In an embodiment, the vacuum is created between an inner dam 152 and outer dam 132 so that the wound 160 is not subjected to the vacuum, but rather the surrounding skin 162. In this embodiment, the outer dam 132 may surround a region 4 inches by 4 inches, for example. The inner dam 152 may surround a region 3 inches by 3 inches for example. At 2.5 psi, the inner dam 152 and liquid impermeable region 124 are pushed away from the skin by a force of 2.5 psi times 9 square inches or 22.5 pounds. A full or partial vacuum drawn in the space between the inner dam 152 and outer dam 132 will be forced inward at between 14.7 psi and something less, such as 10 psi. The area of the region between the two dams 132 and 152 is approximately 16 square inches minus 9 square inches or 7 square inches. Assuming a loss of 2 square inches to dam or gasket material, the space between the inner and outer dam is approximately 5 square inches. With the 10 psi of a partial vacuum exerted on this space, the bandage 120 is held against the skin by a force of 50 pounds, twice the force of that exerted by the blood on the center of the bandage 120, thus, even an imperfect bandage 120 or vacuum will firmly hold to the skin 162 and provide hemostasis. The area of the region covering the wound 160 is sized, relative to the area of the region between the inner and outer dams so that the vacuum force always overcomes the blood pressure force and keeps the bandage 120 against the skin 162. The inner dam 132 can be sized to encase a wound of practically any size from 0.25 inches in length to a full limb amputation, which may be 10 or more inches in diameter. The region interior to the inner dam 132 can be pressurized to assist with hemostasis control even though a vacuum is being drawn to keep the bandage 120 in place, as long as the net pressure force does not exceed the net vacuum hold-down force.

The port 180 communicating between the space between the inner dam 152 and outer dam 132 through the fluid impermeable region 124 or membrane connecting the dams to a region outside the bandage 120 is connected to a vacuum generation device such as a bulb with one or more one-way valves, or another type of vacuum pump. The vacuum port 180 further comprises a vacuum valve 182, which prevents disabling of the vacuum but may be opened to relieve the vacuum when desired. The strap 166 is optional in this embodiment but can assist in positioning the bandage 120 and keeping a good seal with the skin 162 while the vacuum is being generated. The vacuum therefore generates all or some of the force holding the bandage 120 to the skin 162. The bandage 120 further preferably comprises a delivery channel for the vacuum or vacuum manifold 184, which is optional, so that the region between the two dams 132 and 152 does not collapse and prevent full distribution of the vacuum. The vacuum port 180 is in fluid communication with the inner lumen of the vacuum manifold 184, if the vacuum manifold 184 is used. The vacuum manifold 184 is a structure, such as a perforated tube that is operably connected to the vacuum port 180 and will not collapse under application of the vacuum and will allow the vacuum to be exerted evenly around the region between the two dams 132 and 152. In the embodiment where the vacuum manifold 184 is not used, the vacuum port 180 is in direct fluid communication with the region between the two dams 132 and 152.

Figure 19:
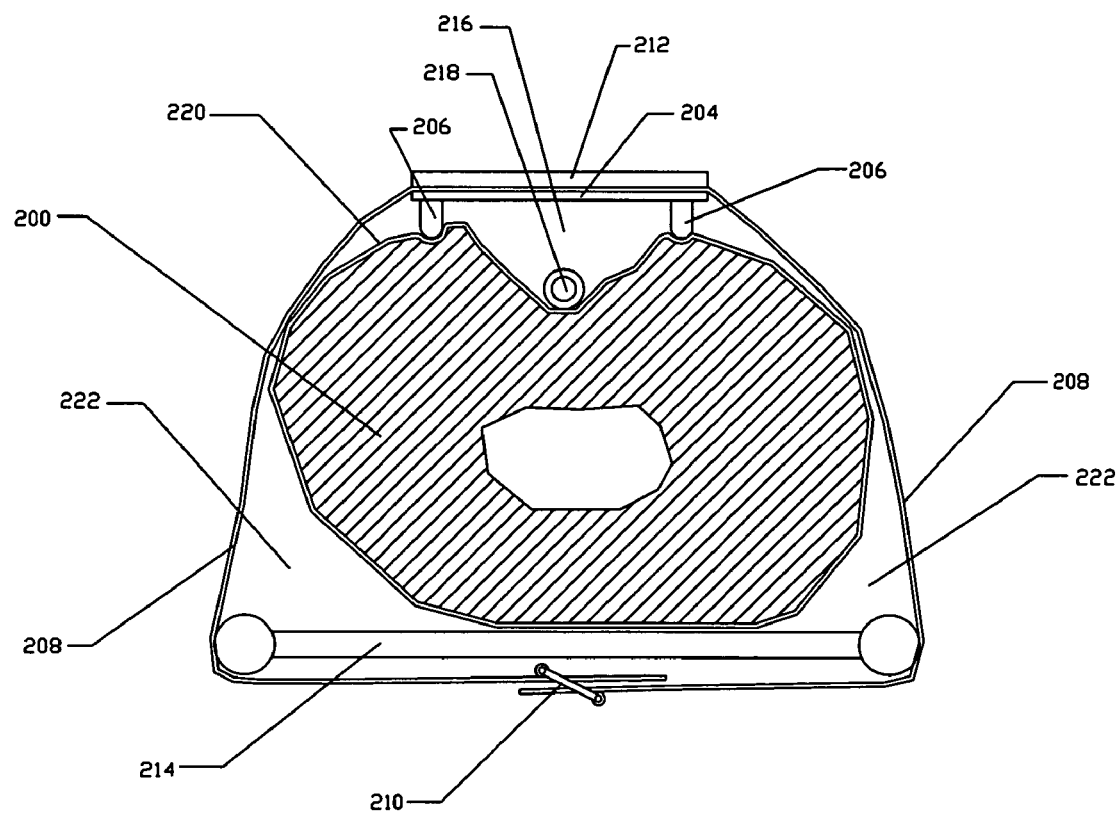
FIG. 19 illustrates a cross-sectional view of an appendage with a wound and a bandage, or PHW, attached thereto. The bandage includes a standoff to prevent a tourniquet effect to the limb, according to aspects of the invention.

FIG. 19 illustrates a cross-sectional view of a limb or appendage 200 with a bandage 202 affixed thereto. The bandage 202 comprises a fluid impermeable region 204, a dam 206, a strap 208, a fastener 210, a scrim 212, and a standoff 214. The body appendage 200 further comprises a wound 216, a severed blood vessel 218, and skin 220. A space 222 exists between the strap 208 and the appendage 200.

Referring to FIG. 19, the standoff 214 prevents the strap 208 from tightly encircling the limb or body appendage 200 in such a way that a tourniquet effect is created, thus preventing the flow of blood to tissues distal to the bandage 202 or the return of venous blood from the region anatomically distal to the bandage 202. The strap 208 is pulled tightly enough that the component of the force exerted by the strap 206 on the dam 206 that forces the strap 206 into the skin 220 is sufficient to overcome systemic arterial pressure. Generally one or two straps 206 are required. By creating spaces or gaps 222 along the side of the limb 200 between the limb 200 and the strap 206, pressure forces created by the strap 206 do not prevent the flow of blood through vasculature within the limb 200. The fastener 210 is a buckle or hook-and-loop material such as Velcro and may further comprise a lever to create a mechanical advantage to increase tightness of the strap 206 around the limb 200. The strap 206 is fabricated from woven or knitted materials including but not limited to polyester, nylon, cotton, polyurethane, combinations of the aforementioned, or the like. The strap 206 may further be a bolt or rigid member fabricated from polymer or metal with telescoping or foreshortening and locking apparatus or means. A threaded bolt traversing the standoff 214 and the scrim 212 is tightened by use of a threaded nut exterior to the standoff 214, the scrim 212 or both. The scrim 212 is a stiffening member that is either fully rigid, partially rigid, or flexible so as to bend outside the plane of the scrim 212. The scrim 212, however, is inelastic and will not deform within the plane of the scrim 212. The standoff 214 is generally rigid or semi-rigid and preferably comprises padding on the surface that comes into contact with the limb 200. The fluid impermeable region 204 and the dam 206 are generally fabricated from soft, elastomeric materials such as but not limited to, C-Flex, polyurethane, silicone elastomer, hydrogel, or the like. In this embodiment, the force holding the bandage 202 against the skin is substantially non-radially distributed, but is, instead, along only one axis.

Figure 20:
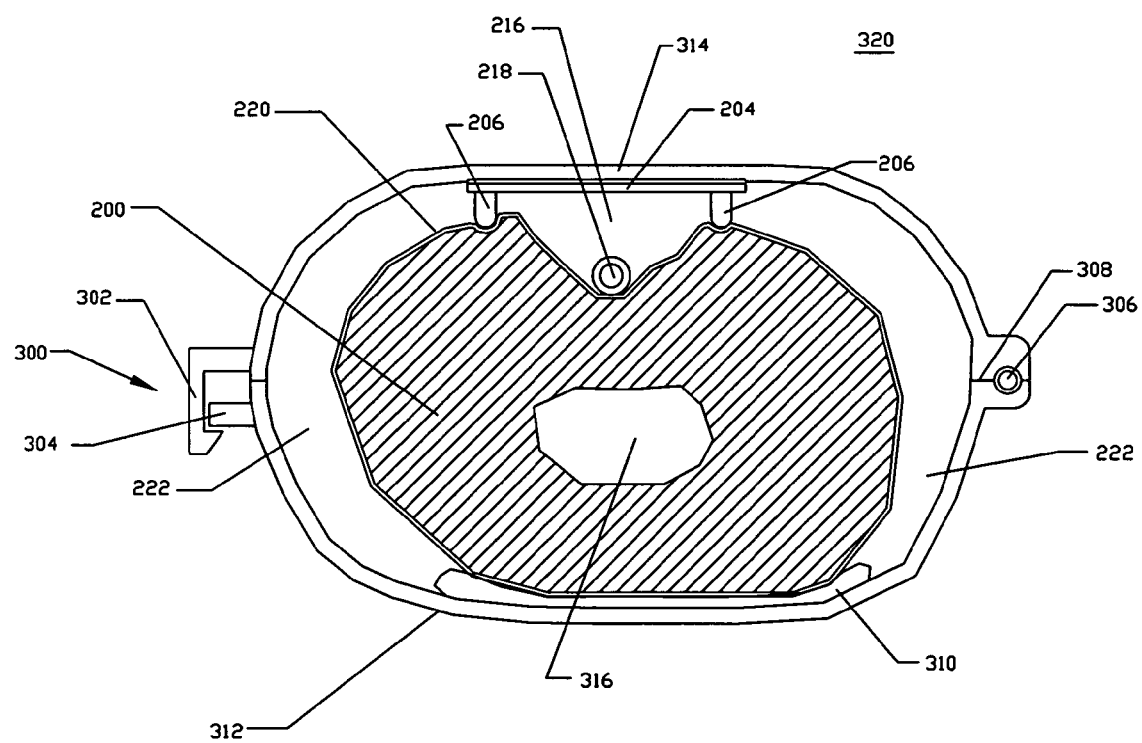
FIG. 20 illustrates a cross-sectional view of an appendage with a wound and a peripheral hemostasis system attached thereto. The peripheral hemostasis system includes a rigid or semi-rigid cuirass to apply a fluid-tight barrier over the wound without creating a tourniquet effect, according to aspects of the invention.

FIG. 20 illustrates another embodiment of the peripheral hemostasis system 320 further comprising an upper shell member 314, a lower shell member 312, a hinge 306, a separation line 308, a latch 300 further comprising a tab 302 and a catch 304, a dam 206, an optional pad 310, and a fluid impermeable barrier 204. The peripheral hemostasis system 320 is wrapped around a limb 200 further comprising a bone 316, a blood vessel 218, a wound 216, and a skin layer 220. A gap 222 exists in at least one circumferential region between the limb 200 and the shell halves 312 and 314.

Referring to FIG. 20, the upper shell member 314 and the lower shell member 312 are rigid or semi-rigid structures that are rotatably affixed to each other by the hinge 306. The upper shell member 314 abuts the lower shell member 312 at the separation line 308, which exists on the hinge 306 side and the latch 300 side, when the shell 320 is closed around limb 200. This type of device 320 is also known as a cuirass. The fluid impermeable barrier 204 and the dams 206 surrounding the barrier 204 are affixed to the inner aspect of the upper shell member 314. The pad 310 is affixed to the interior aspect of the lower shell member 312. The latch 300 is preferably formed integrally to the upper shell member 314 and the lower shell member 312 and is a simple snap latch. Other latches 300 include, but are not limited to, snaps, buckles, zippers, buttons, Velcro, pushbutton latches, slide latches, bayonet catches, screw fixation, and the like.

The upper shell member 314 and the lower shell member 312 are fabricated by injection molding, metal forming, die stamping, blow molding, laminating, or the like, using materials including, but not limited to, thermoplastics, steel, aluminum, polysulfine, polystyrene, polyethylene, polyester, polycarbonate, polyvinyl chloride, and the like. The latch 300 components 302 and 304 are similarly fabricated and are either integral to the upper and lower shell members 314 and 312 or they are separately fabricated and affixed using adhesives, screws, rivets, or the like. Provision for size adjustability can be made with the peripheral hemostasis system 320 using, for example, internal cinches and straps, different thickness padding 310, variable catch locations on the latch 300, a multi position hinge 306, and the like. The peripheral hemostasis system 320 creates a closure and sealing force directed substantially along only one axis. The peripheral hemostasis system 320 does not, in this embodiment, create uniform radially inwardly directed forces that completely circumnavigate the appendage, a situation that could reduce venous return blood flow and cause a tourniquet effect.

The peripheral hemostasis system 320 is provided opened and in a container which is sealed from contamination. The peripheral hemostasis system 320 is preferably sterilized using ethylene oxide, gamma radiation, electron beam irradiation, or the like prior to use. A single or double aseptic pouch, such as one fabricated from Tyvek, is a preferred container for the peripheral hemostasis system 320. The peripheral hemostasis system 320 is removed from its aseptic container and placed around the limb 200 so that the dams 206 impinge on the skin 220 surrounding the wound 216. The upper shell member 314 is brought into apposition with the lower shell member 312 and the latch 300 is engaged making sure a tight seal occurs between the dam 206 and the skin 220. Thus, blood escaping from the blood vessel 218 cannot escape the environs of the wound 218 and the patient cannot bleed to death. At the minimum, blood loss is greatly slowed minimizing the chance of bleeding to death during transport to a medical facility. The space 222 between the shell parts 314 and 312 and the limb 200 make sure that force is only applied in one direction to the limb. Force in the orthogonal direction is not applied so a complete seal is not created around the limb 200. Thus, the potential for venous return being compromised is reduced and the tourniquet effect is eliminated or reduced.

The present invention is suitable for wounds to many parts of the body. The external hemostatic pack works on the arms, the legs, the head, a finger, the torso, etc. The present invention also describes a fluid or liquid-impermeable band-aid type device with the further enhancement that a fluid-tight dam is comprised within the device to prevent blood loss out the side of the band-aid. The dam, in a preferred embodiment, does not use adhesives to attach or seal to the body, but rather is attached with mechanical locks and straps since adhesives often fail in a wet or contaminated environment. The dam and liquid impermeable wound covering part of the bandage are preferably conformable to different body curves but still retain the substantial part of their width and length when applied. The dam and liquid impermeable region further are configured to prevent or minimize distortion, wrinkling, kinking, or the like. Such prevention of distortion, wrinkling, or kinking is accomplished, in a preferred embodiment by the use of stiffeners laterally disposed across the bandage to prevent lateral compression. These stiffeners allow for flexibility but provide column strength to prevent lateral collapse of the bandage. In yet another embodiment, the hemostatic packing device is filled through a valved port operably connected to the region inside the dam and underneath the liquid impermeable barrier. The hemostatic packing device is pressurized with fluids such as air, water, antibiotic material, saline, and the like. Such pressurization to levels at or above systemic arterial pressure assists in even distribution of said pressure and is capable of further assisting with hemostasis.

The present invention includes apparatus and methods for treating wounds. The present invention, and the means described herein for accomplishing said wound treatment, may be embodied in other specific forms without departing from its spirit or essential characteristics. For example, although the preferred embodiment comprises a sterile bandage or packing device in an aseptic transfer package, a non-sterile device may also be appropriate in certain instances. Further, the strap means, used to hold the fluid impermeable barrier and dams against the skin, may be replaced with a rigid or semi-rigid shell, split to form a hinged or connected pair of clamshells which may be opened and then closed and locked around an appendage. The shell is, in one embodiment, a pair of "C" shaped members forming a bracelet. The shell could be square and the blood seal be tightened with a plate and a jackscrew with a handle or knob. This shell, or cuirass, is able to force the fluid impermeable barrier and dams, pre-mounted to a rigid or semi-rigid backbone, frame, or scrim, against the patient to force the dams into the skin without causing the tourniquet effect of a tightly wrapped strap. Thrombogenic or antimicrobial agents could be applied to any region of the peripheral hemostasis system. Adjustment means, such as a jackscrew or a lever and ratchet is used to control the amount of force with which the dams are impressed into the skin to cause the fluid-tight seal. The described embodiments are to be considered in all respects only as illustrative and not restrictive. The scope of the invention is therefore indicated by the appended claims rather than the foregoing description. All changes that come within the meaning and range of equivalency of the claims are to be embraced within their scope.

What is claimed is:

1. An apparatus adapted to prevent hemorrhage from a skin-penetrating wound in a human body comprising:
    a liquid impermeable region that covers the wound,
    a strap to which the liquid impermeable region is affixed to hold said liquid impermeable region over said wound without the use of adhesives,
    at least one dam or gasket, which seals the liquid impermeable region to the skin of the human body without the use of adhesives,
    a locking device to affix the strap to the human body and force the at least one dam or gasket against the skin with enough force to prevent blood leakage therefrom,
    wherein the area inside the at least one dam, the liquid impermeable region, and the skin around the wound form a cavity from which blood cannot escape under systemic arterial pressure, and
    a packing device centrally disposed on the liquid impermeable region, wherein said packing device exerts pressure to the wound to minimize hemorrhage, and wherein the packing device comprises a sealed, expandable chamber and an inflation device to fill said sealed, expandable chamber with liquid or gas.

2. The apparatus of claim 1 wherein at least one dam seals against the skin comprising the periphery of said wound by a pressure seal.

3. The apparatus of claim 1 wherein said strap generates enough force to provide a hemostatic pressure seal between at least one dame and the skin.

4. The apparatus of claim 1 comprising a plurality of dams.

5. The apparatus of claim 1 wherein said plurality of dams are interconnected by at least two shunt dams that forms at least two compartments between the dams.

6. The apparatus of claim 1 further comprising a flexible, substantially inelastic scrim that underlies the dam and fluid impermeable region.

7. An apparatus adapted to prevent hemorrhage from a skin-penetrating wound in a human body comprising:
- a liquid impermeable region that covers the wound,
- a strap to which the liquid impermeable region is affixed to hold said liquid impermeable region over said wound without the use of adhesives,
- at least one dam or gasket, which seals the liquid impermeable region to the skin of the human body without the use of adhesives,
- a locking device to affix the strap to the human body and force the at least one dam or gasket against the skin with enough force to prevent blood leakage therefrom,
- wherein the area inside the at least one dam, the liquid impermeable region, and the skin around the wound form a cavity from which blood cannot escape under systemic arterial pressure, and
- a rigid collar that extends about at least a portion of the appendage where the wound is being treated and over which the bandage is wrapped, wherein the rigid collar does not come between the liquid impermeable region and dam and the patient's skin, further wherein the rigid collar is larger in size than the appendage so that it does not touch the appendage at substantially all points along the interior surface of the collar.

8. The apparatus of claim 7 wherein the locking device comprises a hook and loop material.

9. The apparatus of claim 7 comprising a plurality of dams.

10. The apparatus of claim 9 wherein said plurality of dams forms a pattern of concentric or nested structures.

11. The apparatus of claim 10 wherein the region between the nested structures comprises thrombogenic material.

12. The apparatus of claim 7, further comprising a flexible, substantially inelastic scrim that underlies the dam and fluid impermeable region.

13. The apparatus of claim 7 wherein said dam seals against the skin comprising the periphery of said wound by a pressure seal.

14. The apparatus of claim 7 wherein said strap generates enough force to provide a hemostatic pressure seal between the at least one dam and the skin.

15. An apparatus adapted to prevent hemorrhage from a skin-penetrating wound in a human body comprising:
- a liquid impermeable region that covers the wound,
- a strap to which the liquid impermeable region is affixed to hold said liquid impermeable region over said wound without the use of adhesives,
- a plurality of dams or gaskets, which seal the liquid impermeable region to the skin of the human body without the use of adhesives, and
- a locking device to affix the strap to the human body and force the dams or gaskets against the skin with enough force to prevent blood leakage therefrom,
- wherein the area inside the dams or gaskets, the liquid impermeable region, and the skin around the wound form a cavity from which blood cannot escape under systemic arterial pressure, and wherein a vacuum is drawn on the region between two nested dams or gaskets to hold the dams or gaskets against the patient.

16. A method of minimizing hemorrhage from a skin-penetrating wound to the extremity of a mammal comprising the steps of:
- placing a liquid impermeable region over the wound such that dams at or near the periphery of said liquid impermeable region rest outside the wound but against the skin;
- wrapping a strap, affixed to said liquid impermeable region, around the extremity to hold the dams surrounding the liquid impermeable region against the skin surrounding the wound to the extremity;
- tightening the strap to force the dams into the skin;
- locking the straps to each other to maintain the straps around the extremity; and
- drawing a vacuum in the region between two of the dams to assist in holding the dams against the skin.

17. The method of claim 16 further comprising the step of applying thrombogenic material to the region between the dams.

18. A method of minimizing hemorrhage from a skin-penetrating wound to the extremity of a mammal comprising the steps of:
- placing a liquid impermeable region over the wound such that dams at or near the periphery of said liquid impermeable region rest outside the wound but against the skin;
- wrapping a strap, affixed to said liquid impermeable region, around the extremity to hold the dams surrounding the liquid impermeable region against the skin surrounding the wound to the extremity;
- tightening the strap to force the dams into the skin;
- locking the straps to each other to maintain the straps around the extremity; and
- applying a semi-rigid or rigid C-Bracelet to the extremity to minimize a tourniquet effect caused by the tight straps, wherein the C-Bracelet does not completely touch the extremity and effectively squeezes the dams against the extremity only in one direction.

19. The method of claim 18, further comprising the step of applying a temporary adhesive edge, affixed to at least one end of the strap, to the skin to aid in placement and control of the liquid impermeable region over the wound.

20. The method of claim 18, wherein the liquid impermeable region comprises at least two nested or concentric dams, and further comprising the step applying thrombogenic material to the region between the dams.

* * * * *